(12) United States Patent
Adams et al.

(10) Patent No.: US 8,648,174 B2
(45) Date of Patent: Feb. 11, 2014

(54) UCP4

(71) Applicant: Genentech, Inc., South San Francisco, CA (US)

(72) Inventors: Sean Adams, Belmont, CA (US); James Pan, Foster City, CA (US); Alan Zhong, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/672,232

(22) Filed: Nov. 8, 2012

(65) Prior Publication Data

US 2013/0066052 A1 Mar. 14, 2013

Related U.S. Application Data

(63) Continuation of application No. 13/236,459, filed on Sep. 19, 2011, now Pat. No. 8,313,927, which is a continuation of application No. 11/265,966, filed on Nov. 3, 2005, now Pat. No. 8,067,229, which is a continuation-in-part of application No. 09/397,342, filed on Sep. 15, 1999, now abandoned.

(60) Provisional application No. 60/129,674, filed on Apr. 16, 1999, provisional application No. 60/114,223, filed on Dec. 30, 1998, provisional application No. 60/101,279, filed on Sep. 22, 1998.

(51) Int. Cl.
*C07K 16/18* (2006.01)
*C07K 16/44* (2006.01)
*C07K 19/00* (2006.01)

(52) U.S. Cl.
USPC ............ 530/387.3; 530/387.9; 530/388.1; 530/388.15; 530/388.2; 530/391.1; 530/391.3; 530/391.7; 530/866; 530/867

(58) Field of Classification Search
None
See application file for complete search history.

(56) References Cited

U.S. PATENT DOCUMENTS

| | | | |
|---|---|---|---|
| 4,775,662 A | 10/1988 | Gleason et al. | |
| 5,010,010 A | 4/1991 | Gautvik et al. | |
| 5,407,810 A | 4/1995 | Builder et al. | |
| 5,663,304 A | 9/1997 | Builder et al. | |
| 7,001,742 B1 * | 2/2006 | Liu et al. | 435/69.1 |
| 2005/0043520 A1 | 2/2005 | Baker et al. | |

FOREIGN PATENT DOCUMENTS

| | | |
|---|---|---|
| EP | 307247 | 3/1989 |
| WO | WO 96/33735 A1 * | 10/1996 |
| WO | 98/31396 | 7/1998 |
| WO | 98/52958 | 11/1998 |

OTHER PUBLICATIONS

Altschul et al., "Local alignment statistics" Methods in Enzymology 266:460-480 (1996).
Attwood, TK The babel of bioinformatics, Science, 290:471-473, (Oct. 20, 2000).
Bolivar et al.,"Construction and Characterization of New Cloning Vehicles. II. A Multipurpose Cloning System" Gene 2:95-113 (1977).
Boss et al., "Uncoupling protein-3: a new member of the mitochondrial carrier family with tissue-specific expression" FEBS Letters 408(1):39-42 (May 12, 1997).
Bouillaud et al., "Molecular approach to thermogenesis in brown adipose tissue: cDNA cloning of the mitochondrial uncoupling protein" Proc. Natl. Acad. Sci. USA 82(2):445-448 (Jan. 1985).
Cassard et al., "Human uncoupling protein gene: structure, comparison with rat gene, and assignment to the long arm of chromosome 4" Journal of Cellular Biochemistry 43(3):255-264 (Jul. 1990).
Fleury et al.,"Uncoupling protein-2: a novel gene linked to obesity and hyperinsulinemia" Nature Genetics 15(3):269-272 (Mar. 1997).
Gibson et al., "A novel method for real time quantitative RT-PCR" Genome Research 6(10):995-1001 (Oct. 1996).
Gimeno et al., "Cloning and characterization of an uncoupling protein homolog: a potential molecular mediator of human thermogenesis" Diabetes 46(5):900-906 May 1997).
Gong et al., "Uncoupling protein-3 is a mediator of thermogenesis regulated by thyroid hormone, β 3-adrenergic agonists, and leptin" Journal of Biological Chemistry 272(39):24129-24132 (Sep. 26, 1997).
Gonzalez-Barroso et al., "Activation of the uncoupling protein by fatty acids is modulated by mutations in the C-terminal region of the protein" European Journal of Biochemistry 239(2):445-450 (Jul. 15, 1996).
Gura, T., "Uncoupling proteins provide new clue to obesity's causes" Science 280(5368): 1369-1370 May 29, 1998).
Harper et al., "Mitochondrial uncoupling proteins as potential targets for pharmacological agents". Current Opin. in Pharmacol, 4:603-607, (2004).
Heid et al., "Real time quantitative PCR" Genome Research 6(10):986-994 (Oct. 1996).
Holmes et al., "Structure and Functional Expression of a Human Interleukin-8 Receptor" Science 253(5025):1278-1280 (Sep. 13, 1991).
Jacobsson et al., "Mitochondrial uncoupling protein from mouse brown fat. Molecular cloning, genetic mapping, and mRNA expression" Journal of Biological Chemistry 260(30):16250-16254 (Dec. 25, 1985).

(Continued)

*Primary Examiner* — Ron Schwadron
(74) *Attorney, Agent, or Firm* — Gates & Cooper LLP

(57) ABSTRACT

The present invention is directed to novel polypeptide, designated in the present application as "UCP4" (SEQ ID NO: 1), having homology to certain human uncoupling proteins ("UCPs") and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention, and methods for producing the polypeptides of the present invention.

12 Claims, 11 Drawing Sheets

(56) References Cited

OTHER PUBLICATIONS

Klaus et al., "Physiology of transgenic mice with brown fat ablation: obesity is due to lowered body temperature" American Journal of Physiology 274(2 Pt 2):R287-R293 (Feb. 1998).

Liu et al., "Uncoupling protein-3: a muscle-specific gene upregulated by leptin in ob/ob mice" Gene 207:1-7 (Jan. 19, 1998).

Mao et al., "UCP4, a novel brain-specific mitochondrial protein that reduces membrane potential in mammalian cells" FEBS Letters 443(3):326-330 (Jan. 29, 1999).

Mayinger et al., "Labeling of two different regions of the nucleotide binding site of the uncoupling protein from brown adipose tissue mitochondria with two ATP analogs" Biochemistry 31(43):10536-10543 (Nov. 3, 1992).

Nicholls et al., "Thermogenic mechanisms in brown fat" Physiological Reviews 64(1):1-64 (Jan. 1984).

Ott, L., An Introduction to Statistical Methods and Data Analysis, 3rd edition, Boston: PWS-Kent Publishing Co. (1988).

Ruppert et al., "Cloning and Expression of Human $TAF_{II}250$: a TBP-associated Factor Implicated in Cell-cycle Regulation" Nature 362:175-179 (1993).

Salvioli et al., "JC-1, but not $DiOC_6(3)$ or rhodamine 123, is a reliable fluorescent probe to assess $\Delta\Psi$ changes in intact cells: implications for studies on mitochondrial functionality during apoptosis" FEBS Letters 411(1):77-82 (Jul. 7, 1997).

Smiley et al., "Intracellular heterogeneity in mitochondrial membrane potentials revealed by a J-aggregate-forming lipophilic cation JC-1" Proc., Natl. Acad. Sci. USA 88(9):3671-3675 (May 1, 1991).

Solanes et al., "The human uncoupling protein-3 gene. Genomic structure, chromosomal localization, and genetic basis for short and long form transcripts" Journal of Biological Chemistry 272(41):25433-25436 (Oct. 10, 1997).

Surwit et al., "Differential effects of fat and sucrose on the development of obesity and diabetes in C57BL/6J and A/J mice", Metabolism 44(5):645-651 (May 1995).

Thimmappaya et al., "Adenovirus VAI RNA is required for efficient translation of viral mRNAs at late times after infection" Cell 31(3 Pt 2):543-551 (Dec. 1982).

Vidal-Puig et al., "UCP3: an uncoupling protein homologue expressed preferentially and abundantly in skeletal muscle and brown adipose tissue" Biochemical & Biophysical Research Communications 235(1):79-82 (Jun. 9, 1997).

Wolf G., "A new uncoupling protein: a potential component of the human body weight regulation system" Nutrition Reviews 55(5):178-179 (May 1997).

\* cited by examiner

MSVPEEERLLPLLTQRWPRASKFLLSGCAATVAELATFPLDLTKTRLQMQGEAALARLG
DGARESAPYRGMVRTALGIIEEEGFLKLWQGVTPAIYRHVVYSGGRMVTYEHLREVVFG
KSEDEHYPLWKSVIGGMMAGVIGQFLANPTDLVKVQMQMEGKRKLEGKPLRFRGVHHAF
AKILAEGGIRGLWAGWVPNIQRAALVNMGDLTTYDTVKHYLVLNTPLEDNIMTHGLSSL
CSGLVASILGTPADVIKSRIMNQPRDKQGRGLLYKSSTDCLIQAVQGEGFMSLYKGFLP
SWLRMTPWSMVFWLTYEKIREMSGVSPF

FIG. 1

CCGAGCTCGGATC
CCGTTATCGTCTTGCGCTACTGCTGA
ATGTCCGTCCCGGAGGAGGAGGAGAGGCTTTTGCCGCTGACCCAGAGATGGCCCGAGCG
AGCAAATTCCTACTGTCCCGGCTGCGCGGCTACCGTGGCCGAGCTAGCAACCTTTCCCTG
GATCTCACAAAAACTCGACTCCAAATGCAAGGAGAAGCAGCTCTTGCTCGTTGGGAGAC
GGTGCAAGAGAATCTGCCCCCTATAGGGGAATGGTGCGCACAGCCCTAGGGATCATTGAA
GAGGAAGGCTTTCTAAAGCTTTGGCAAGGAGTGACACCCGCCATTTACAGACACGTAGTG
TATTCTGAGGTCGAATGGTCACATATGAAACATCTCCGAGAGGTTGTGTTTGGCAAAAGT
GAAGATGAGCATTATCCCTTTGGAAATCAGTCATTGGAGGGATGATGCAAATGCTGGTGTTATT
GGCCAGTTTTTAGCCAATCCAACTAGTGAAGGTTCAGATGCAAATGCAAATGGGAAGGAAAA
AGGAAACTGGAAGGAAGAAAACCATTGGCGATTTCGTGGTGTACATCATGCATTTGCAAAAATC
TTAGCTGAAGGAGGAATACGAGAGGCTTTGGGCAGGCTGGGTACCCAATATACAAAGAGCA
GCACTGGTGAATATGGGAGATTTAACCACTTATGATGAAACACTTGGTATTG
AATACACCACTTGAGGACGACAATATCATGACTCACGGTTTATCAAGTTTATGTTCTGGACTG
GTAGCTTCTATTCTGGGAACACCAGCGATGTCATCAAAAGCAGAATAATCATCGACTGCTTGATTCAGGCT
CGAGATAAACAAGGAAGGGACTTTTGTATAAATCATCGACTGCTTGATTCAGGCT
GTTCAAGGTGAAGGATTCATGAGTCTATATAAAGGCTTTTTTACCATCTGGCTGAGAATG
ACCCCTGGTCAATGGTGTTCTGCTTACTTATGAAAAATCAGAGAGATGAGTGGAGTC
AGTCCATTTTTAAGAATTCTGCAGATATCCATCACACTGGC

FIG. 2

```
UCP1   1  -------MGGLTASDVHPTLGVQLFSAPIAACLADVITFPLDTAKVRLQVQ
UCP2   1  -------MVGFKATDVPPTATVKFLGAGTAACIADLITFPLDTAKVRLQIQ
UCP3   1  -------MAVKFLGAGTAACFADLVTFPLDTAKVRLQIQ
UCP4   1  MSVPEEEERLPLTQRWPRASKFLLSGCAATVAELATFPLDTKTRLQMQ
                                              ******* * * **
                                                    I

UCP1  45  GECP------TSSVIRYKGVLGTITAVVKTEGRMKLYSGLPAGLQRQIS
UCP2  45  GESQGPVR---ATVSAQYRGVMGTILTMVRTEGPRSLYNGLVAGLQRQMS
UCP3  33  GENQ-AVQ---TARLVQYRGVLGTILTMVRTEGPCSPYNGLVAGLQRQMS
UCP4  51  GEAALARLGDGARESAPYRGMVRTALGIEEEGFLKLWQGVTPAIYRHVV
                                                        II

UCP1  88  SASLRIGLYDTVQEFLTAGKET-APSLGSKILAGLTTGGVAVFIGQPTEV
UCP2  92  FASVRIGLYDSVKQFYTKGSE--HASIGSRLLAGSTTGALAVAVAQPTDV
UCP3  79  FASIRIGLYDSVKQVYTPKGAD-NSSLTTRILAGCTTGAMAVTCAQPTDV
UCP4 101  YSGGRMVTYEHLREVFGKSEDEHYPLWKSVIGGMMAGVIGQFLANPTDL
                                                ***  *
                                                  III

UCP1 137  VKVRLQAQSHLHG--IKPRYTGTYNAYRIIATTEGLTGLWKGTTPNLMRS
UCP2 140  VKVRFQAQARAG---GGRRYQSTVNAYKTIAREEGFRGLWKGTSPNVARN
UCP3 128  VKVRFQASIHLGPSRSDRKYSGTMDAYRTIAREEGVRGLWKGTLPNIMRN
UCP4 151  VKVQMQMEGKRKLEGKPLRFRGVHHAFAKILAEGGIRGLWAGWVPNIQRA
          ****                                        *
```

FIG. 3A

```
UCP1 185  V T I N C T E L V T Y D L M K E A F V K N N I L A D D V P C H L V S A L I A G F C A T A M S S P V D
UCP2 187  A I V N C A E L V T Y D L I K D A L L K A N L M T D D L P C H F T S A F G A G F C T T V I A S P V D
UCP3 178  A I V N C A E V T Y D I L K E K L L D Y H L L T D N F P C H F V S A F G A G F C A T V V A S P V D
UCP4 201  A L V N M G D E T Y D T V K H Y L V L N T P L E D N I M T H G L S S L C S G L V A S I L G T P A D
                                                                                                    * *

UCP1 235  V V K T R F I N S P P G Q - - - - - Y K S V P N C A M K V F T N E G P T A F F K G L V P S F L R L
UCP2 237  V V K T R Y M N S A L G Q - - - - - Y S S A G H C A L T M L Q K E G P R A F Y K G F M P S F L R L
UCP3 228  V V K T R Y N N S P P G Q - - - - - Y F S P L D C M I K M V A Q E G P T A F Y K G F T P S F L R L
UCP4 251  V I K S R I M N Q P R D K Q G R G L L Y K S S T D C L I Q A V Q G E G F M S L Y K G F L P S W L R M
          * *                                                                                  VI

UCP1 279  G S W N V I M F V C F E Q L K R E L S K R Q T M D C A T
UCP2 281  G S W N V V M F V T Y E Q L K R A L M A A C T S R E A P F
UCP3 272  G S W N V V M F V T Y E Q L K R A L M K V Q M L R E S P F
UCP4 301  T P W S M V F W L T Y E K I R E M S G V S P F - - - - -

FIG. 3B
```

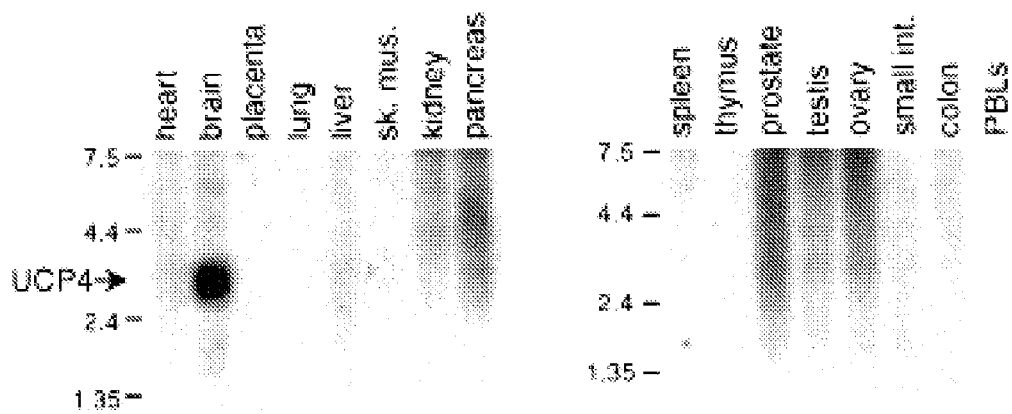
FIG. 4A  FIG. 4B
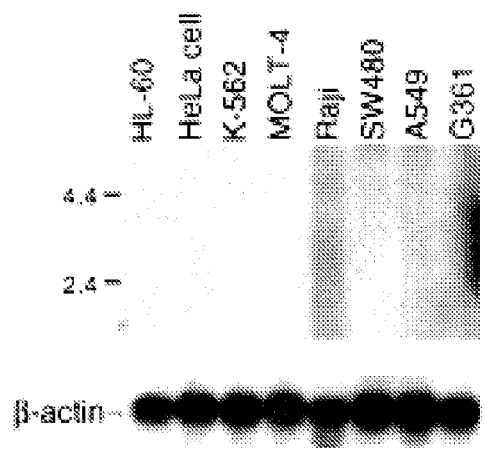 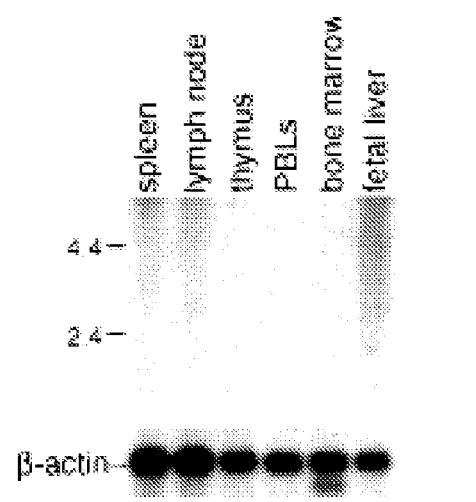
FIG. 4C  FIG. 4D anti-cyto anti-cyto   anti-flag anti-flag anti-cyto anti-cyto   anti-flag anti-flag

```
CGTTATCGTCTTGGCGCTACTGCTGAATGTCCGTCCCGGAGGAGGAGGAGAGGCTTTTGCCGCTGACCCAGAG
ATGGCCCCGAGCGAGCAAATTCCTACTGTCCGGCTGCGCGGCTACCGTGGCCGAGCTAGCAACCTTTCCCCTG
GATCTCACAAAACTCGACTCAAATGCAAGGAGAAGCAGTCTTGCTCGTTGGGAGACGGTGCAAGAGAAT
CTGCCCCTATAGGGGAATGGTGCGCACAGACACGTAGTTATTTCTGGAGGTCGAATGGTCACATATGAACATCTCCGA
AGGAGTGACACCCGCCATTTACAGACAGCGTAGTTATTTCTGGAGGTCGAATGGTCACATATGAACATCTCCGA
GAGGTTGTGTTTGGCAAAGTGAAGATGAGCATTATCCCCTTTGGAAATCAGTCATTGGAGGGATGATGGCTG
GTGTTATTGGCCAGTTTTTAGCCAATCCAACTGGCGATTTCGTGGTGTACATCATGCAAAATCTTAGCTGAAGGAGGAATA
ACTGGAAGGAAAACCATTGCGATTTCGTGGTGTACATCATGCAAAATCTTAGCTGAAGGAGGAATA
CGAAGGCTTTGGGCAGGCTGGGTACCCAATATACAAGAGCAGCACTGGTGAATATGGAGATTTAACCACTT
ATGATACAGTGAAACACTACTGGTATTGAATACACCACTGAGGACAATATCATGACTCACGTTTATCAAG
TTTATGTTCTGGACTGGTAGCTTCTATTCTGGGAACACCAGCACCGCGATGTCATCAAAAGCAGAATAATGAATCAA
CCACGAGATAAACAAGGAAGGGGACTTTGTATAAATCATGACTGGCTGACTGCTGATTCAGGCTGTTCAGGTG
AAGGATTCATGAGTCTATATAAGGCTTTTACCATCTTGGCTGGAGAATGACCCCTTGGTCAATGGTGTTCTG
GCTTACTTATGAAAAATCAGAGAGATGAGTGGGCATCTGCAACACATACCCCTAAAGATGCAACCCTTAAA
GATACAGTGTTCAGTATTATTGAAATATGGGACTATTTGAAATATGGGGCATCTGCAACACATACCCCTAAAGATGCAACCCTTAAA
AGACACCTATTCCACAGAGACTGATTTATAGGGGCAGCACTTTATTTTTCTGAAACCCAAGTTCTCTTT
GACTCCTCTTTTGTCCAAAAGTGATCTGGTCGATCTCACAAGGCCATCCAATGAGACCCCGNACAGCATTT
TCTAAAGA
```

FIG. 7

UCP4

RELATED APPLICATIONS

This is a non-provisional application filed under 37 CFR 1.53(b) claiming priority to and is a continuation of application Ser. No. 13/236,459, filed Sep. 19, 2011, now U.S. Pat. No. 8,313,927, issued Nov. 20, 2012, which is a continuation of application Ser. No. 11/265,966, filed Nov. 3, 2005, now U.S. Pat. No. 8,067,229, issued Nov. 29, 2011, which is a continuation of application Ser. No. 09/397,342, filed Sep. 15, 1999, now abandoned, which claims the benefit of U.S. Provisional Application Nos. 60/129,674, filed Apr. 16, 1999, 60/114,223, filed Dec. 30, 1998, and 60/101,279, filed Sep. 22, 1998, the contents of which are incorporated herein by reference.

SEQUENCE LISTING

Incorporated herein by reference in its entirety is a Sequence Listing named "SEQ_TXT.txt", comprising SEQ ID NO:1 through SEQ ID NO:18, which include nucleic acid and/or amino acid sequences disclosed herein. The Sequence Listing was submitted on Nov. 8, 2012 in ASCII text format via EFS-Web, and thus constitutes both the paper and computer readable form thereof. The Sequence Listing was created using FastSEQ 4.0 on Jun. 22, 2012, and is 16 KB in size.

FIELD OF THE INVENTION

The present invention relates generally to the identification and isolation of novel DNA having homology to certain human uncoupling proteins, and to the recombinant production of novel polypeptides, designated herein as "uncoupling protein 4" or "UCP4."

BACKGROUND OF THE INVENTION

Uncoupling proteins or "UCPs", believed to play a role in the metabolic process, have been reported in the literature. UCPs were first found and described in the brown fat cells of hibernating animals, such as bears. UCPs were believed to help such hibernators and other cold-weather adapted animals maintain core body temperatures in cold weather by raising their body's resting metabolic rate. Because humans possess relatively small quantities of brown adipose tissue, UCPs were originally thought to play a minor role in human metabolism.

Several different human uncoupling proteins have now been described. [See, generally, Gura, *Science*, 280:1369-1370 (1998)]. The human uncoupling protein referred to as UCP1 was identified by Nicholls et al. Nicholls et al. showed that the inner membrane of brown fat cell mitochondria was very permeable to proteins, and the investigators traced the observed permeability to a protein, called UCP1, in the mitochondrial membrane. Nicholls et al. reported that the UCP1, by creating such permeability, reduced the number of ATPs that can be made from a food source, thus raising body metabolic rate and generating heat. [Nicholls et al., *Physiol. Rev.*, 64, 1-64 (1984)].

It was later found that UCP1 is indeed expressed only in brown adipose tissue [Bouillaud et al., *Proc. Natl. Acad. Sci.*, 82:445-448 (1985); Jacobsson et al., *J. Biol. Chem.*, 260:16250-16254 (1985)]. Genetic mapping studies have shown that the human UCP1 gene is located on chromosome 4. [Cassard et al., *J. Cell. Biochem.*, 43:255-264 (1990)].

Another human UCP, referred to as UCPH or UCP2, has also been described. [Gimeno et al., *Diabetes*, 46:900-906 (1997); Fleury et al., *Nat. Genet.*, 15:269-272 (1997); Boss et al., *FEBS Letters*, 408:39-42 (1997); see also, Wolf, *Nutr. Rev.*, 55:178-179 (1997)]. Fleury et al. teach that the UCP2 protein has 59% amino acid identity to UCP1, and that UCP2 maps to regions of human chromosome 11 which have been linked to hyperinsulinaemia and obesity. [Fleury et al., supra]. It has also been reported that UCP2 is expressed in a variety of adult tissues, such as brain and muscle and fat cells. [Gimeno et al., supra, and Fleury et al., supra].

A third human UCP, UCP3, was recently described in Boss et al., supra; Vidal-Puig et al., *Biochem. Biophys. Res. Comm.*, 235:79-82 (1997); Solanes et al., *J. Biol. Chem.*, 272:25433-25436 (1997); and Gong et al., *J. Biol. Chem.*, 272:24129-24132 (1997). [See also Great Britain Patent No. 9716886]. Solanes et al. report that unlike UCP1 and UCP2, UCP3 is expressed preferentially in human skeletal muscle, and that the UCP3 gene maps to human chromosome 11, adjacent to the UCP2 gene. [Solanes et al., supra]. Gong et al. describe that the UCP3 expression can be regulated by known thermogenic stimuli, such as thyroid hormone, beta3-andrenergic agonists and leptin. [Gong et al., supra].

SUMMARY OF THE INVENTION

A cDNA clone (DNA 77568-1626) has been identified, having certain homologies to some known human uncoupling proteins, that encodes a novel polypeptide, designated in the present application as "UCP4."

In one embodiment, the invention provides an isolated nucleic acid molecule comprising DNA encoding a UCP4 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a UCP4 polypeptide comprising the sequence of amino acid residues from about 1 to about 323, inclusive of FIG. 1 (SEQ ID NO:1), or (b) the complement of the DNA molecule of (a).

In another aspect, the invention concerns an isolated nucleic acid molecule encoding a UCP4 polypeptide comprising DNA hybridizing to the complement of the nucleic acid between about nucleotides 40 and about 1011 inclusive, of FIG. 2 (SEQ ID NO: 2). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the cDNA in ATCC Deposit No. 203134, or (b) the complement of the DNA molecule of (a). In a preferred embodiment, the nucleic acid comprises a DNA encoding the same mature polypeptide encoded by the cDNA in ATCC Deposit No. 203134.

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from about 1 to about 323, inclusive of FIG. 1 (SEQ ID NO:1), or the complement of the DNA of (a).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 to about 323, inclusive of FIG. 1 (SEQ ID NO:1), or (b) the complement of the DNA of (a).

Further embodiments of the invention are directed to fragments of the UCP4 coding sequence, which are sufficiently long to be used as hybridization probes. Preferably, such fragments contain at least about 20 to about 80 consecutive bases included in the sequence of FIG. 2 (SEQ ID NO:2). Optionally, such fragments include the N-terminus or the C-terminus of the sequence of FIG. 2 (SEQ ID NO:2).

In another embodiment, the invention provides a vector comprising DNA encoding UCP4 or its variants. The vector may comprise any of the isolated nucleic acid molecules hereinabove defined.

A host cell comprising such a vector is also provided. By way of example, the host cells may be CHO cells, *E. coli*, or yeast. A process for producing UCP4 polypeptides is further provided and comprises culturing host cells under conditions suitable for expression of UCP4 and recovering UCP4 from the cell culture.

In another embodiment, the invention provides isolated UCP4 polypeptide encoded by any of the isolated nucleic acid sequences hereinabove defined.

In a specific aspect, the invention provides isolated native sequence UCP4 polypeptide, which in one embodiment, includes an amino acid sequence comprising residues 1 to 323 of FIG. 1 (SEQ ID NO:1).

In another aspect, the invention concerns an isolated UCP4 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 to about 323, inclusive of FIG. 1 (SEQ ID NO:1).

In a further aspect, the invention concerns an isolated UCP4 polypeptide, comprising an amino acid sequence scoring at least about 80% positives, preferably at least about 85% positives, more preferably at least about 90% positives, most preferably at least about 95% positives when compared with the amino acid sequence of residues 1 to 323 of FIG. 1 (SEQ ID NO:1).

In yet another aspect, the invention concerns an isolated UCP4 polypeptide, comprising the sequence of amino acid residues 1 to about 323, inclusive of FIG. 1 (SEQ ID NO:1), or a fragment thereof sufficient to, for instance, provide a binding site for an anti-UCP4 antibody. Preferably, the UCP4 fragment retains at least one biological activity of a native UCP4 polypeptide.

In a still further aspect, the invention provides a polypeptide produced by (i) hybridizing a test DNA molecule under stringent conditions with (a) a DNA molecule encoding a UCP4 polypeptide having the sequence of amino acid residues from about 1 to about 323, inclusive of FIG. 1 (SEQ ID NO: 1), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In another embodiment, the invention provides chimeric molecules comprising a UCP4 polypeptide fused to a heterologous polypeptide or amino acid sequence. An example of such a chimeric molecule comprises a UCP4 polypeptide fused to an epitope tag sequence or a Fc region of an immunoglobulin.

In another embodiment, the invention provides an antibody which specifically binds to UCP4 polypeptide. Optionally, the antibody is a monoclonal antibody.

In yet another embodiment, the invention concerns agonists and antagonists of a native UCP4 polypeptide. In a particular embodiment, the agonist or antagonist is an anti-UCP4 antibody.

In a further embodiment, the invention concerns a method of identifying agonists or antagonists of a native UCP4 polypeptide, comprising contacting the native UCP4 polypeptide with a candidate molecule and monitoring the desired activity. The invention also provides therapeutic methods and diagnostic methods using UCP4.

In a still further embodiment, the invention concerns a composition comprising a UCP4 polypeptide, or an agonist or antagonist as hereinabove defined, in combination with a carrier.

BRIEF DESCRIPTION OF THE DRAWINGS

FIG. 1 shows the derived amino acid sequence of native sequence UCP4 SEQ ID NO:1.

FIG. 2 shows the nucleotide sequence of a cDNA encoding native sequence UCP4 SEQ ID NO:2.

FIGS. 3A-3B show an amino acid sequence alignment of UCP4 SEQ ID NO: 1 with other known uncoupling proteins, UCP1 (SEQ ID NO: 16), UCP2 (SEQ ID NO:17), and UCP3 (SEQ ID NO:18). The six putative transmembrane domains are shown and are underlined (and labeled I to VI, respectively). The asterisks (*) shown below the protein sequence indicate three (3) putative mitochondrial carrier protein motifs. A putative nucleotide binding domain is double underlined.

FIGS. 4A-4H show the results of Northern blot analysis. Human adult tissues and brain tissues (Clontech), in addition to peripheral blood leukocytes (PBLs), cancer cells, and fetal tissues, were probed with UCP4 cDNA. The figures illustrate that the UCP4 transcript was detected in human brain tissues, spinal cord, medulla, corpus callosum, and substantia nigra.

FIG. 7 shows a "from DNA" sequence assembled from selected EST sequences SEQ ID NO: 5.

DETAILED DESCRIPTION OF THE PREFERRED EMBODIMENTS

I. Definitions

Figure 4E:
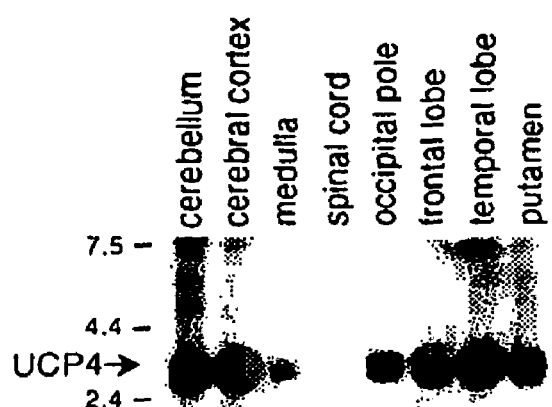
Figure 4F:
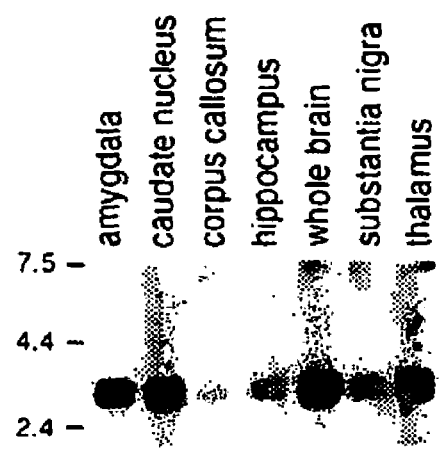

The terms "UCP4 polypeptide", "UCP4 protein" and "UCP4" when used herein encompass native sequence UCP4 and UCP4 variants (which are further defined herein). The UCP4 may be isolated from a variety of sources, such as from human tissue types or from another source, or prepared by recombinant and/or synthetic methods.

A "native sequence UCP4" comprises a polypeptide having the same amino acid sequence as a UCP4 derived from nature. Such native sequence UCP4 can be isolated from nature or can be produced by recombinant and/or synthetic means. The term "native sequence UCP4" specifically encompasses naturally-occurring truncated or soluble forms, naturally-occurring variant forms (e.g., alternatively spliced forms) and naturally-occurring allelic variants of the UCP4. In one embodiment of the invention, the native sequence UCP4 is a mature or full-length native sequence UCP4 comprising amino acids 1 to 323 of FIG. 1 (SEQ ID NO:1).

"UCP4 variant" means anything other than a native sequence UCP4, and includes UCP4 having at least about 80% amino acid sequence identity with the amino acid sequence comprising residues 1 to 323 of the UCP4 polypeptide sequence shown in FIG. 1 (SEQ ID NO:1). Such UCP4 variants include, for instance, UCP4 polypeptides wherein one or more amino acid residues are added, or deleted, at the N- or C-terminus, as well as within one or more internal domains, of the sequence of FIG. 1 (SEQ ID NO:1). Ordinarily, a UCP4 variant will have at least about 80% amino acid sequence identity, more preferably at least about 85% amino acid sequence identity, even more preferably at least about 90% amino acid sequence identity, and most preferably at least about 95% sequence identity with the amino acid sequence comprising residues 1 to 323 of FIG. 1 (SEQ ID NO:1).

"Percent (%) amino acid sequence identity" with respect to the UCP4 sequences identified herein is defined as the percentage of amino acid residues in a candidate sequence that are identical with the amino acid residues in the UCP4 sequence, after aligning the sequences and introducing gaps, if necessary, to achieve the maximum percent sequence identity, and not considering any conservative substitutions as part of the sequence identity. % identity can be determined by WU-BLAST-2, obtained from [Altschul et al., Methods in Enzymology, 266: 460-480 (1996)]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, "percent (%) nucleic acid sequence identity" is defined as the percentage of nucleotides in a candidate sequence that are identical with the nucleotides in the UCP4 coding sequence. The identity values can be generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the UCP4 natural environment will not be present. Ordinarily, however, isolated polypeptide will be prepared by at least one purification step.

An "isolated" nucleic acid molecule encoding a UCP4 polypeptide is a nucleic acid molecule that is identified and separated from at least one contaminant nucleic acid molecule with which it is ordinarily associated in the natural source of the UCP4-encoding nucleic acid. An isolated UCP4-encoding nucleic acid molecule is other than in the form or setting in which it is found in nature. Isolated nucleic acid molecules therefore are distinguished from the UCP4-encoding nucleic acid molecule as it exists in natural cells. However, an isolated nucleic acid molecule encoding a UCP4 polypeptide includes UCP4-encoding nucleic acid molecules contained in cells that ordinarily express UCP4 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-UCP4 monoclonal antibodies (including agonist, antagonist, and neutralizing antibodies) and anti-UCP4 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a UCP4 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of UCP4 which retain the biologic and/or immunologic activities of native or naturally-occurring UCP4. A preferred activity is the ability to affect mitochondrial membrane potential in a way that results in an up- or down-regulation of metabolic rate and/or heat production. One such activity includes the generation of proton leakage in mitochondrial membrane that results in an increase in metabolic rate. The activity may be measured or quantitated in vitro or in vivo.

The term "antagonist" is used in the broadest sense, and includes any molecule that partially or fully blocks, inhibits, or neutralizes a biological and/or immunological activity of a native UCP4 polypeptide disclosed herein. In a similar manner, the term "agonist" is used in the broadest sense and includes any molecule that mimics a biological and/or immunological activity of a native UCP4 polypeptide disclosed herein. Suitable agonist or antagonist molecules specifically include agonist or antagonist antibodies or antibody fragments, immunoadhesins of UCP4 polypeptides, or fragments or amino acid sequence variants of native UCP4 polypeptides.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

II. Compositions and Methods of the Invention

A. Full-Length UCP4

The present invention provides newly identified and isolated nucleotide sequences encoding polypeptides referred to in the present application as UCP4. In particular, cDNA encoding a UCP4 polypeptide has been identified and isolated, as disclosed in further detail in the Examples below. For sake of simplicity, in the present specification the protein encoded by DNA 77568-1626 as well as all further native homologues and variants included in the foregoing definition of UCP4, will be referred to as "UCP4," regardless of their origin or mode of preparation.

As disclosed in the Examples below, a clone DNA 77568-1626 has been deposited with ATCC. The actual nucleotide sequence of the clone can readily be determined by the skilled artisan by sequencing of the deposited clone using routine methods in the art. The predicted amino acid sequence can be determined from the nucleotide sequence using routine skill. For the UCP4 herein, Applicants have identified what is believed to be the reading frame best identifiable with the sequence information available at the time of filing.

Using the Megalign DNASTAR computer program (and algorithms and parameters in this software set by the manufacturer) (Oxford Molecular Group, Inc.), it has been found that a full-length native sequence UCP4 (shown in FIG. 1 and SEQ ID NO:1) has about 34% amino acid sequence identity with UCP3, about 33% amino acid sequence identity with UCP2, and about 29% amino acid sequence identity with UCP1. Accordingly, it is presently believed that UCP4 disclosed in the present application is a newly identified member of the human uncoupling protein family and may possess activity(s) and/or property(s) typical of that protein family, such as the ability to enhance or suppress metabolic rate by affecting mitochondrial membrane potential.

B. UCP4 Variants

In addition to the full-length native sequence UCP4 polypeptides described herein, it is contemplated that UCP4 variants can be prepared. UCP4 variants can be prepared by introducing appropriate nucleotide changes into the UCP4 DNA, and/or by synthesis of the desired UCP4 polypeptide. Those skilled in the art will appreciate that amino acid changes may alter post-translational processes of the UCP4, such as changing the number or position of glycosylation sites or altering the membrane anchoring characteristics.

Variations in the native full-length sequence UCP4 or in various domains of the UCP4 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the UCP4 that results in a change in the amino acid sequence of the UCP4 as compared with the native sequence UCP4. Optionally the variation is by substitution of at least one amino acid with any other amino acid in one or more of the domains of the UCP4. Guidance in determining which amino acid residue may be inserted, substituted or deleted without adversely affecting the desired activity may be found by comparing the sequence of the UCP4 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and, if desired, testing the resulting variants for activity in assays known in the art or as described herein.

One embodiment of the invention is directed to UCP4 variants which are fragments of the full length UCP4. Preferably, such fragments retain a desired activity or property of the full length UCP4.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the UCP4 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of UCP4

Covalent modifications of UCP4 are included within the scope of this invention. One type of covalent modification includes reacting targeted amino acid residues of a UCP4 polypeptide with an organic derivatizing agent that is capable of reacting with selected side chains or the N- or C-terminal residues of the UCP4. Derivatization with bifunctional agents is useful, for instance, for crosslinking UCP4 to a water-insoluble support matrix or surface for use in the method for purifying anti-UCP4 antibodies, and vice-versa. Commonly used crosslinking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the UCP4 polypeptide included within the scope of this invention comprises altering the native glycosylation pattern of the polypeptide. "Altering the native glycosylation pattern" is intended for purposes herein to mean deleting one or more carbohydrate moieties found in native sequence UCP4 (either by removing the underlying glycosylation site or by deleting the glycosylation by chemical and/or enzymatic means), and/or adding one or more glycosylation sites that are not present in the native sequence UCP4. In addition, the phrase includes qualitative changes in the glycosylation of the native proteins, involving a change in the nature and proportions of the various carbohydrate moieties present.

Addition of glycosylation sites to the UCP4 polypeptide may be accomplished by altering the amino acid sequence. The alteration may be made, for example, by the addition of, or substitution by, one or more serine or threonine residues to the native sequence UCP4 (for O-linked glycosylation sites). The UCP4 amino acid sequence may optionally be altered through changes at the DNA level, particularly by mutating the DNA encoding the UCP4 polypeptide at preselected bases such that codons are generated that will translate into the desired amino acids.

Another means of increasing the number of carbohydrate moieties on the UCP4 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the UCP4 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of UCP4 comprises linking the UCP4 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The UCP4 of the present invention may also be modified in a way to form a chimeric molecule comprising UCP4 fused to another, heterologous polypeptide or amino acid sequence.

In one embodiment, such a chimeric molecule comprises a fusion of the UCP4 with a tag polypeptide which provides an epitope to which an anti-tag antibody can selectively bind. The epitope tag is generally placed at the amino- or carboxyl-terminus of the UCP4. The presence of such epitope-tagged forms of the UCP4 can be detected using an antibody against the tag polypeptide. Also, provision of the epitope tag enables the UCP4 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the UCP4 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a UCP4 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

The UCP4 of the invention may also be modified in a way to form a chimeric molecule comprising UCP4 fused to a leucine zipper. Various leucine zipper polypeptides have been described in the art. See, e.g., Landschulz et al., *Science*, 240:1759 (1988); WO 94/10308; Hoppe et al., *FEBS Letters*, 344:1991 (1994); Maniatis et al., *Nature*, 341:24 (1989). Those skilled in the art will appreciate that the leucine zipper may be fused at either the 5' or 3' end of the UCP4 molecule.

D. Preparation of UCP4

The description below relates primarily to production of UCP4 by culturing cells transformed or transfected with a vector containing UCP4 nucleic acid. It is, of course, contemplated that alternative methods, which are well known in the art, may be employed to prepare UCP4. For instance, the UCP4 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the UCP4 may be chemically synthesized separately and combined using chemical or enzymatic methods to produce the full-length UCP4.

1. Isolation of DNA Encoding UCP4

DNA encoding UCP4 may be obtained from a cDNA library prepared from tissue believed to possess the UCP4 mRNA and to express it at a detectable level. Accordingly, human UCP4 DNA can be conveniently obtained from a cDNA library prepared from human tissue, such as described in the Examples. The UCP4-encoding gene may also be obtained from a genomic library or by oligonucleotide synthesis.

Libraries can be screened with probes (such as antibodies to the UCP4 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding UCP4 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra, and are described above in Section I.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using publicly available computer software programs (set to default parameters) such as BLAST, BLAST2, ALIGN, DNAstar, and INHERIT to measure identity or positives for the sequence comparison.

Nucleic acid having protein coding sequence may be obtained by screening selected cDNA or genomic libraries using the deduced amino acid sequence disclosed herein, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for UCP4 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for UCP4-encoding vectors. *Saccharomyces cerevisiae* is a commonly used lower eukaryotic host microorganism.

Suitable host cells for the expression of glycosylated UCP4 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/– DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding UCP4 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The UCP4 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the UCP4-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 μm plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the UCP4-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene, present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the UCP4-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding UCP4.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

UCP4 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the UCP4 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the UCP4 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding UCP4.

Still other methods, vectors, and host cells suitable for adaptation to the synthesis of UCP4 in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence UCP4 polypeptide or against a synthetic peptide based on the DNA sequences provided herein or against exogenous sequence fused to UCP4 DNA and encoding a specific antibody epitope.

5. Purification of Polypeptide

Forms of UCP4 may be recovered from culture medium or from host cell lysates. If membrane-bound, it can be released from the membrane using a suitable detergent solution (e.g. Triton-X 100) or by enzymatic cleavage. Cells employed in expression of UCP4 can be disrupted by various physical or chemical means, such as freeze-thaw cycling, sonication, mechanical disruption, or cell lysing agents.

It may be desired to purify UCP4 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the UCP4. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular UCP4 produced.

E. Uses for UCP4

Nucleotide sequences (or their complement) encoding UCP4 have various applications in the art of molecular biology, including uses as hybridization probes, in chromosome and gene mapping and in the generation of anti-sense RNA and DNA. UCP4 nucleic acid will also be useful for the preparation of UCP4 polypeptides by the recombinant techniques described herein.

The full-length native sequence UCP4 gene (described in Example 1; SEQ ID NO:2), or fragments thereof, may be used as, among other things, hybridization probes for a cDNA library to isolate the full-length UCP4 gene or to isolate still other genes (for instance, those encoding naturally-occurring variants of UCP4 or UCP4 from other species) which have a desired sequence identity to the UCP4 sequence disclosed in FIG. 1 (SEQ ID NO:1). Optionally, the length of the probes will be about 20 to about 80 bases. The hybridization probes may be derived from the nucleotide sequence of SEQ ID NO:2 or from genomic sequences including promoters, enhancer elements and introns of native sequence UCP4. By way of example, a screening method will comprise isolating the coding region of the UCP4 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the UCP4 gene of the present invention can be used to screen libraries of human cDNA, genomic DNA or mRNA to determine which members of such libraries the probe hybridizes to. Hybridization techniques are described in further detail in the Examples below.

Fragments of UCP4 DNA contemplated by the invention include sequences comprising at least about 20 to 30 consecutive nucleotides of the DNA of SEQ ID NO:2. Preferably, such sequences comprise at least about 50 consecutive nucleotides of the DNA of SEQ ID NO:2.

The probes may also be employed in PCR techniques to generate a pool of sequences for identification of closely related UCP4 coding sequences.

Nucleotide sequences encoding a UCP4 can also be used to construct hybridization probes for mapping the gene which encodes that UCP4 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for UCP4 encode a protein which binds to another protein, the UCP4 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor UCP4 can be used to isolate correlative ligand(s). Screening assays can be designed to find lead compounds that mimic the biological activity of a native UCP4 or a receptor for UCP4. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode UCP4 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding UCP4 can be used to clone genomic DNA encoding UCP4 in accordance with established techniques and the genomic sequences used to generate transgenic animals that contain cells which express DNA encoding UCP4. Methods for generating transgenic animals, particularly animals such as mice or rats, have become conventional in the art and are described, for example, in U.S. Pat. Nos. 4,736,866 and 4,870,009. Typically, particular cells would be targeted for UCP4 transgene incorporation with tissue-specific enhancers. Transgenic animals that include a copy of a transgene encoding UCP4 introduced into the germ line of the animal at an embryonic stage can be used to examine the effect of increased expression of DNA encoding UCP4. Such animals can be used as tester animals for reagents thought to confer protection from, for example, pathological conditions associated with its overexpression or underexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of UCP4 can be used to construct a UCP4 "knock out" animal which has a defective or altered gene encoding UCP4 as a result of homologous recombination between the endogenous gene encoding UCP4 and altered genomic DNA encoding UCP4 introduced into an embryonic cell of the animal. For example, cDNA encoding UCP4 can be used to clone genomic DNA encoding UCP4 in accordance with established techniques. A portion of the genomic DNA encoding UCP4 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the UCP4 polypeptide.

Nucleic acid encoding the UCP4 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

It is believed that the UCP4 gene therapy has applications in, for instance, treating metabolic conditions. This can be accomplished, for example, using the techniques described above and by introducing a viral vector containing a UCP4 gene into certain tissues (like muscle or fat) to increase metabolic rate in these targeted tissues and thereby elevate energy expenditure.

Generally, methods of treatment employing UCP4 are contemplated by the invention. Fuel combustion, electron transport, proton pumping and $O_2$ consumption (which may be referred to collectively as metabolic rate) are coupled to ATP synthesis. There can be an "inefficiency" in mammals, such that a portion of metabolic rate (in some cases which may be greater than 20%) may be ascribed to $H^+$ "leak" back into the matrix space with no ATP synthesis.

It is believed UCP4 may be involved in catalyzing $H^+$ leak, thereby playing a role in energetic inefficiency in vivo. Accordingly, modulating UCP4 activity or quantities (presence) of UCP4 in mammalian tissues (particularly, metabolically important tissues), may concomitantly modulate $H^+$ leak, metabolic rate and heat production. The methods of modulating (either in an up-regulation or down-regulation mode) metabolic rate in a mammal has a variety of therapeutic applications, including treatment of obesity and the symptoms associated with stroke, trauma (such as burn trauma), sepsis and infection.

In the treatment of obesity, those skilled in the art will appreciate that the modulation of mitochondrial membrane potential may be used to increase body metabolic rate, thereby enhancing an individual's ability for weight loss. Screening assays may be conducted to identify molecules which can up-regulate expression or activity (such as the uncoupling) of UCP4. The molecules thus identified can then be employed to increase metabolic rate and enhance weight loss. The UCP4 polypeptides are useful in assays for identifying lead compounds for therapeutically active agents that modulate expression or activity of UCP4. Candidate molecules or compounds may be assayed with the mammals' cells or tissues to determine the effect(s) of the candidate molecule or compound on UCP4 expression or activity. Such screening assays may be amenable to high-throughput screening of chemical libraries, and are particularly suitable for identifying small molecule drug candidates. Small molecules include but are not limited to synthetic organic or inorganic compounds. The assays can be performed in a variety of formats, including protein-protein binding assays, biochemical screening assays, immunoassays, cell based assays, etc. Such assay formats are well known in the art.

Accordingly, in one embodiment, there is provided a method of conducting a screening assay to identify a molecule which enhances or up-regulates expression of UCP4, comprising the steps of exposing a mammalian cell or tissue sample believed to comprise UCP4 to a candidate molecule and subsequently analyzing expression of UCP4 in said sample. In this method, the sample may be further analyzed for mitochondrial membrane potential. Optionally, the UCP4 is a polypeptide comprising amino acid residues 1 to 323 of FIG. 1 (SEQ ID NO:1). The sample being analyzed may comprise various mammalian cells or tissues, including but not limited to human brain tissue. The candidate molecule employed in the screening assay may be a small molecule comprising a synthetic organic or inorganic compound. In an alternative embodiment, the screening assay is conducted to identify a molecule which decreases or down-regulates expression of UCP4. The effect(s) that such candidate molecule may have on the expression and/or activity or UCP4 may be compared to a control or reference sample, such as for instance, expression or activity of UCP4 observed in a like mammal.

UCP4 may also be employed in diagnostic methods. For example, the presence or absence of UCP4, or alternatively over- or under-expression of UCP4 in an individual's cells or tissues, can be detected using assays known in the art, including those described in the Examples below. Thus, the invention also provides a method of detecting expression of UCP4 in a mammalian cell or tissue sample, comprising contacting a mammalian cell or tissue sample with a DNA probe and analyzing expression of UCP4 mRNA transcript in said sample. The sample may comprise various mammalian cells or tissues, including but not limited to, human brain tissue. The skilled practitioner may use information resulting from such detection assays to assist in predicting metabolic conditions or risk for onset of obesity. If it is determined, for instance, that UCP4 activity in a patient is abnormally high or low, therapy, such as hormone therapy, could be administered to return the UCP4 activity to a physiologically acceptable state.

Detection of impaired UCP4 function in the mammal may also be used to assist in diagnosing impaired neural activity or neural degeneration. It is presently believed UCP4 may be involved in the regulation of brain temperature or metabolic rate that is required for normal brain function (and associated neural activity). It is also presently believed that UCP4 may control the generation of reactive oxygen species and therefore contribute to neural degeneration. Molecules identified in the screening assays which have been found to suppress UCP4 expression or function may also be employed to treat fever since it is believed that UCP4 is up-regulated during episodes of fever.

F. Anti-UCP4 Antibodies

The present invention further provides anti-UCP4 antibodies. Exemplary antibodies include polyclonal, monoclonal, humanized, bispecific, and heteroconjugate antibodies.

1. Polyclonal Antibodies

The anti-UCP4 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the UCP4 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-UCP4 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the UCP4 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51-631.

The culture medium in which the hybridoma cells are cultured can then be assayed for the presence of monoclonal antibodies directed against UCP4. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-UCP4 antibodies of the invention may further comprise humanized antibodies or human antibodies. Humanized forms of non-human (e.g., murine) antibodies are chimeric immunoglobulins, immnoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

4. Bispecific Antibodies

Bispecific antibodies are monoclonal, preferably human or humanized, antibodies that have binding specificities for at least two different antigens. In the present case, one of the binding specificities is for the UCP4, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been to proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-UCP4 Antibodies

The anti-UCP4 antibodies of the invention have various utilities. For example, anti-UCP4 antibodies may be used in diagnostic assays for UCP4, e.g., detecting its expression in specific cells or tissues. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-UCP4 antibodies also are useful for the affinity purification of UCP4 from recombinant cell culture or natural sources. In this process, the antibodies against UCP4 are immobilized on a suitable support, such a Sephadex resin or filter paper, using methods well known in the art. The immobilized antibody then is contacted with a sample containing the UCP4 to be purified, and thereafter the support is washed with a suitable solvent that will remove substantially all the material in the sample except the UCP4, which is bound to the immobilized antibody. Finally, the support is washed with another suitable solvent that will release the UCP4 from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human UCP4

EST databases, which included public EST databases (e.g., GenBank), and a proprietary EST database (LIFESEQ™, Incyte Pharmaceuticals, Palo Alto, Calif.), were searched for sequences having homologies to human UCP3. The search was performed using the computer program BLAST or BLAST2 [Altschul et al., *Methods in Enzymology,* 266:460-480 (1996)] as a comparison of the UCP3 protein sequences to a 6 frame translation of the EST sequences. Those comparisons resulting in a BLAST score of 70 (or in some cases, 90) or greater that did not encode known proteins were clustered and assembled into consensus DNA sequences with the program AssemblyLIGN and MacVector (Oxford Molecular Group, Inc.).

A DNA sequence ("from DNA") was assembled relative to other EST sequences using AssemblyLIGN software (FIG. 7; SEQ ID NO:5). ESTs from the Incyte database included the sequences having the following accession nos.: 3468504; 3369262; 4220747; 1254733; 5016160; 3770189; 2265329; 928717; 3715961; 3528102; 961523; 1863723; 382533; 918252; 918404; 4313009; 3801604; c-swh06; 3464955; c-lsh09; 090424; 1316891; 1342069; 1435593; 16014011; 1668098; 1668103; 222248; 243244; 246984; 272663; 305678; 305871; 3369262; 3464955; and 3715961. In addition, the from DNA sequence was extended using repeated cycles of BLAST and AssemblyLIGN to extend the sequence as far as possible using the sources of EST sequences discussed above.

Based on this DNA sequence, oligonucleotides were synthesized to isolate a clone of the full-length coding sequences for UCP4 by PCR. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp.

PCR primers (forward and reverse) were synthesized:

```
forward PCR primer
                                          (SEQ ID NO: 3)
CGCGGATCCCGTTATCGTCTTGCGCTACTGC (U401)

reverse PCR primer
                                          (SEQ ID NO: 4)
GCGGAATTCTTAAAATGGACTGACTCCACTCATC (U406)
```

UCP4 with an NH$_2$-terminal Flag-tag also was cloned into pcDNA3 (pcDNA3Flag-UCP4; Invitrogen) between BamHI and EcoRI restriction sites. The following forward and reverse PCR primers were synthesized.

```
forward PCR primer
                                          (SEQ ID NO: 6)
CGCGGATCCGAAATGGACTACAAGGACGACGATG

ACAAGTCCGTCCCGGAGGAGGAGG (U410)

reverse PCR primer
                                          (SEQ ID NO: 4)
GCGGAATTCTTAAAATGGACTGACTCCACTCATC (U406)
```

RNA for construction of the cDNA libraries was isolated from brain tissue. The cDNA libraries used to isolated the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clone isolated by PCR as described above gave the full-length DNA sequence for UCP4 (designated herein as DNA 77568-1626 [FIG. 2, SEQ ID NO: 2] and the derived protein sequence for UCP4.

The entire coding sequence of UCP4 is shown in FIG. 2 (SEQ ID NO:2). Clone DNA 77568-1626 contains a single open reading frame with an apparent translational initiation site at nucleotide positions 40-42, and an apparent stop codon at nucleotide positions 1009-1011. (See FIG. 2; SEQ ID NO:2). The predicted polypeptide precursor is 323 amino acids long. It is presently believed that UCP4 is a membrane-bound protein and contains at least 6 transmembrane regions. These putative transmembrane regions in the UCP4 amino acid sequence are illustrated in FIG. 3. Clone DNA 77568, designated as DNA 77568-1626, contained in the pcDNA3 vector (Invitrogen) has been deposited with ATCC and assigned ATCC deposit no. 203134. UCP4 polypeptide is obtained or obtainable by expressing the molecule encoded by the cDNA insert of the deposited ATCC 203134 vector. Digestion of the deposited ATCC 203134 vector with BamHI and EcoRI restriction enzymes will yield an approximate 972 plus 34 bp insert. The full-length UCP4 protein shown in FIG. 1 has an estimated molecular weight of about 36,061 daltons and a pI of about 9.28.

An alignment of the amino acid sequence of UCP4 with UCPs 1, 2 and 3 is illustrated in FIG. 3. Some notable differences were identified between UCP1 and UCP4. When UCP1 lacks its putative nucleotide binding site, it is resistant to inhibition by nucleotides, and when Phe-267 in UCP1 is substituted with a Tyr residue, UCP1 has enhanced uncoupling activity. [Gonzalez-Barroso et al., *Eur. J. Biochem.*, 239: 445-450 (1996); Mayinger et al., *Biochem.*, 31: 10536-10543 (1992)]. Yet, like UCP2 and UCP3, UCP4 has a Tyr residue at this position. (See FIG. 3). Additionally, the carboxy-terminus of UCP1 has been implicated in the activation of its uncoupling activity by free fatty acids (FFA). Substitution of Cys-305 by Ala or Ser residues results in either decreased or increased activation by FFA, respectively. [Gonzalez-Barroso et al., supra]. Because UCP2 has an Ala-307, UCP3 has a Ser-298, and UCP4 has a Ser-321, the uncoupling activity of UCP4 and the other UCPs is likely regulated differently by nucleotides and FFA.

The human UCP4 gene has been mapped to chromosomal location 6 p11.2-q12 which is closest to genomic marker SHGC-34952.

Example 2

Northern Blot Analysis

Figure 4G:
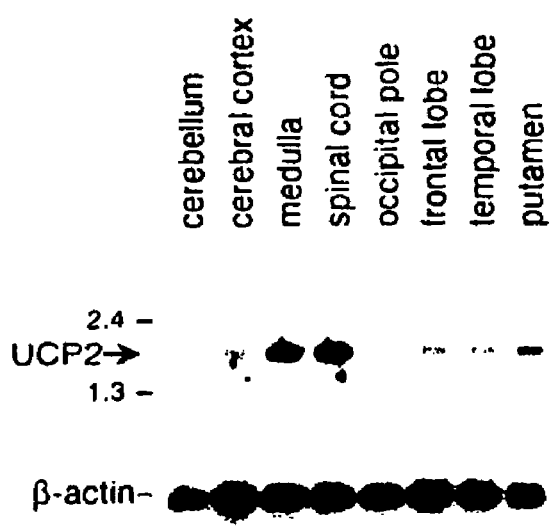

Expression of UCP4 mRNA in human tissues was examined by Northern blot analysis. Human RNA blots were hybridized to a 1 kilobase $^{32}$P-labelled DNA probe based on the full length UCP4 cDNA; the probe was generated by digesting pcDNA3UCP4 and purifying the UCP4 cDNA insert. Human adult RNA blot MTN-II (Clontech) (FIGS. 4A, 4B, 4D, 4E, and 4F), human fetal tissue blot (FIGS. 4D and 4H), PBLs (FIGS. 4B and 4D), and cancer cells (FIG. 4C) were incubated with the DNA probes. As shown in FIG. 4C, the cancer cells probed included HL-60 (promyelocytic leukemia), HeLa cells, K562 (chronic myelogenous leukemia), MOLT-4 (lymphoblastic leukemia), Raji (Burkitt's lymphoma), SW480 (colorectal adenocarcinoma), A549 (lung carcinoma), and G361 (melanoma). The expression of UCP2 was also examined by probing a human brain multiple tissue blot with human UCP2 cDNA. (FIG. 4G). All blots were subsequently probed with a β-actin cDNA.

Northern analysis was performed according to manufacturer's instructions (Clontech). The blots were developed after overnight exposure to x-ray film.

Figure 4H:
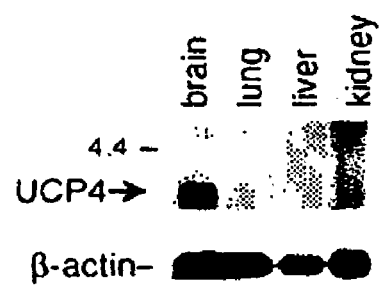

As shown in FIGS. 4A-4H, UCP4 mRNA transcripts were detected. Expression was seen in brain tissues, spinal cord, medulla, corpus callosum, and substantia nigra, but not in the other human tissues or cancer cell lines examined. Although the UCP4 transcript level was higher in brain tissues than in the spinal cord, medulla, corpus callosum, and substantia nigra (FIGS. 4A, 4E, and 4F), the UCP2 transcript levels were higher in the spinal cord and medulla (FIG. 4G). In the human fetal tissue blot, the UCP4 transcript was only detected in the brain. (FIG. 4H).

Example 3

Use of UCP4 as a Hybridization Probe

The following method describes use of a nucleotide sequence encoding UCP4 as a hybridization probe.

DNA comprising the coding sequence of full-length or mature UCP4 (as shown in FIG. 2, SEQ ID NO:2) is employed as a probe to screen for homologous DNAs (such as those encoding naturally-occurring variants of UCP4) in human tissue cDNA libraries or human tissue genomic libraries.

Hybridization and washing of filters containing either library DNAs is performed under the following high stringency conditions. Hybridization of radiolabeled UCP4-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence UCP4 can then be identified using standard techniques known in the art.

Example 4

Expression of UCP4 in *E. coli*

This example illustrates preparation of UCP4 by recombinant expression in *E. coli*.

The DNA sequence encoding UCP4 (SEQ ID NO:2) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will optionally include sequences which encode for an antibiotic resistance gene, a trp promoter, a polyhis leader (including the first six STII codons, polyhis sequence, and enterokinase cleavage site), the UCP4 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. If no signal sequence is present, and the expressed UCP4 is intracellular, the cell pellet obtained by the centrifugation can be solubilized using various agents known in the art, and the solubilized UCP4 protein can then be purified using a metal chelating column under conditions that allow tight binding of the protein. If a signal sequence is present, the expressed UCP4 can be obtained from the cell's periplasm or culture medium. Extraction and/or solubilization of the UCP4 polypeptides can be performed using agents and techniques known in the art. (See e.g. U.S. Pat. Nos. 5,663,304; 5,407,810).

Example 5

Expression of UCP4 in Mammalian Cells

This example illustrates preparation of UCP4 by recombinant expression in mammalian cells.

The vector, pRK5 (see EP 307,247, published Mar. 15, 1989), is employed as the expression vector. Optionally, the UCP4 DNA is ligated into pRK5 with selected restriction enzymes to allow insertion of the UCP4 DNA using ligation methods such as described in Sambrook et al., supra. The resulting vector is called pRK5-UCP4.

In one embodiment, the selected host cells may be 293 cells. Human 293 cells (ATCC CRL 1573) are grown to confluence in tissue culture plates in medium such as DMEM supplemented with fetal calf serum and optionally, nutrient components and/or antibiotics. About 10 µg pRK5-UCP4 DNA is mixed with about 1 µg DNA encoding the VA RNA gene [Thimmappaya et al., *Cell,* 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated, off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of UCP4 polypeptide. The cultures containing transfected cells may undergo further incubation (in serum free medium) and the medium is tested in selected bioassays.

In an alternative technique, UCP4 may be introduced into 293 cells transiently using the dextran sulfate method described by Somparyrac et al., *Proc. Natl. Acad. Sci.,* 12:7575 (1981). 293 cells are grown to maximal density in a spinner flask and 700 µg pRK5-UCP4 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed UCP4 can then be concentrated and purified by any selected method, such as dialysis and/or column chromatography.

In another embodiment, UCP4 can be expressed in CHO cells. The pRK5-UCP4 can be transfected into CHO cells using known reagents such as CaPO, or DEAE-dextran. As described above, the cell cultures can be incubated, and the medium replaced with culture medium (alone) or medium containing a radiolabel such as $^{35}$S-methionine. After determining the presence of UCP4 polypeptide, the culture medium may be replaced with serum free medium. Preferably, the cultures are incubated for about 6 days, and then the conditioned medium is harvested. The medium containing the expressed UCP4 can then be concentrated and purified by any selected method.

Epitope-tagged UCP4 may also be expressed in host CHO cells. The UCP4 may be subcloned out of the pRK5 vector. The subclone insert can undergo PCR to fuse in frame with a selected epitope tag such as a poly-his tag into a Baculovirus expression vector. The poly-his tagged UCP4 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged UCP4 can then be concentrated and purified by any selected method, such as by $Ni^{2+}$-chelate affinity chromatography.

In an alternative method, the UCP4 may be expressed intracellularly (where no signal sequence is employed). This intracellular expression, and subsequent extraction or solubilization and purification may be performed using techniques and reagents known in the art.

Example 6

Expression of UCP4 in Yeast

The following method describes recombinant expression of UCP4 in yeast.

First, yeast expression vectors are constructed for intracellular production or secretion of UCP4 from the ADH2/GAPDH promoter. DNA encoding UCP4 and the promoter is inserted into suitable restriction enzyme sites in the selected plasmid to direct intracellular expression of UCP4. For secretion, DNA encoding UCP4 can be cloned into the selected plasmid, together with DNA encoding the ADH2/GAPDH promoter, a native UCP4 signal peptide or other mammalian signal peptide, or, for example, a yeast alpha-factor or invertase secretory signal/leader sequence, and linker sequences (if needed) for expression of UCP4. Alternatively, the native signal sequence of UCP4 is employed.

Yeast cells, such as *S. cerevisiae* yeast strain AB110, can then be transformed with the expression plasmids described above and cultured in selected fermentation media as set forth, for instance, in U.S. Pat. Nos. 4,775,662 and 5,010,00. The transformed yeast supernatants can be analyzed by precipitation with 10% trichloroacetic acid and separation by SDS-PAGE, followed by staining of the gels with Coomassie Blue stain.

Recombinant UCP4 can subsequently be isolated and purified by removing the yeast cells from the fermentation medium by centrifugation and then concentrating the medium using selected cartridge filters. The concentrate containing UCP4 may further be purified using selected column chromatography resins. In an alternative method, the UCP4 may be expressed intracellularly (where no signal sequence is employed). The intracellular expression, and subsequent extraction or solubilization and purification may be performed using techniques and reagents known in the art.

Example 7

Expression of UCP4 in Baculovirus-Infected Insect Cells

The following method describes recombinant expression of UCP4 in Baculovirus-infected insect cells.

The sequence coding for UCP4 is fused upstream of an epitope tag contained within an expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding UCP4 or the desired portion of the coding sequence of UCP4 is amplified by PCR with primers complementary to the 5' and 3' regions. The 5' primer may incorporate flanking (selected) restriction enzyme sites. The product is then digested with those selected restriction enzymes and subcloned into the expression vector. The vector may contain the native signal sequence for UCP4 if secretion is desired.

Recombinant baculovirus is generated by co-transfecting the above plasmid and BaculoGold™ virus DNA (Pharmingen) into Spodoptera frugiperda ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged UCP4 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 micron filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged UCP4 are pooled and dialyzed against loading buffer.

Alternatively, purification of the IgG tagged (or Fc tagged) UCP4 can be performed using known chromatography techniques, including for instance, Protein A or protein G column chromatography.

Example 8

Measurement of Mitochondrial Membrane Potential Change Induced by UCP4

Assays were conducted to determine the effects of UCP4 expression on mitochondrial membrane potential.

Human embryonic kidney 293 cells (ATCC CRL 1573) were grown in culture medium (DMEM, 10% fetal bovine serum, 2 mM L-glutamine, 100 units/ml penicillin, 100 microgram/ml streptomycin) to 60%-80% confluence in 6-well plates and transiently transfected using FuGene™ 6 transfection reagent (Boehringer Mannheim; according to manufacturer's instructions) with UCP-expressing constructs (pcDNA3UCP4 or pcDNA3UCP3), UCP-expressing constructs with a $NH_2$-terminal Flag-tag (pcDNA3Flag-UCP4 or pcDNA3Flag-UCP3), or vector control (pcDNA3; available from Invitrogen).

The expression constructs for cDNA encoding UCP4 with or without a $NH_2$-terminal Flag-tag were prepared according to Example 1. Expression constructs for cDNA encoding UCP3 were prepared by first obtaining cDNA encoding human UCP3 from a melanoma cDNA library by PCR. PCR primers (forward and reverse) were synthesized:

```
forward PCR primer
                                      (SEQ ID NO: 7)
GCGAAGCTTGCCATGGTTGGACTGAAGCCTTCAGA (U301)

reverse PCR primer
                                      (SEQ ID NO: 8)
CGCGAATTCTCAAAACGGTGATTCCCGTAACAT (U302)
```

The expression construct for cDNA encoding UCP3 with a $NH_2$-terminal Flag-tag was prepared by the following PCR primers.

```
forward PCR primer
                                      (SEQ ID NO: 9)
GCGAAGCTTGCCATGGACTACAAGGACGACGATGACAAG

GTTGGACTGAAGCCTTCAGACG (U303)

reverse PCR primer
                                      (SEQ ID NO: 8)
CGCGAATTCTCAAAACGGTGATTCCCGTAACAT (U302)
```

UCP3 with or without the $NH_2$-terminal Flag-tag were cloned into pcDNA3 (pcDNA3UCP3 and pcDNA3Flag-UCP3) between HindIII and EcoRI sites and confirmed by DNA sequencing. Flag-tagged UCP3 and UCP4 expressed in 293 cells were detected by Western blot analysis using anti-Flag M2 monoclonal antibody (Kodak) and ECL detection kit (Pierce).

Mitochondrial membrane potential was analyzed according to methods known in the art. [Salvioli et al., *FEBS Lett.*, 411: 77-82 (1997); Smiley et al., *Proc. Natl. Acad. Sci. USA*, 88: 3671-3675 (1991)]. About 24-36 hours post-transfection, cells were trypsinized, and $1.5 \times 10^6$ were pelleted by centrifugation. The pelleted cells were resuspended in 0.5 ml of a JC-1 dye solution and incubated in the presence or absence of 50 μm CCCP (carbonylcyanide m-chlorophenylhydrazone; Sigma) in the dark for 30 minutes at 37° C. JC-1 (5,5',6,6'-tetrachloro-1,1',3,3'-tetraethylbenzimidazolcarbocyanine iodide; Molecular Probes, Eugene, Oreg.) is a membrane potential sensitive, fluorescent dye. To prepare the dye solution, JC-1 was first prepared as a stock solution in dimethyl sulfoxide (DMSO; Sigma) at a concentration of 5 mg/ml. The stock solution was diluted to 1 mg/ml with DMSO, and then further diluted to 10 μg/ml with culture medium prewarmed to 37° C. and filtered through both 0.45 μm and 0.2 μm filters to exclude aggregated JC-1.

The stained cells were washed and resuspended in 1.0 ml culture medium. The cells resuspended in culture medium were examined by spectrofluorometry (RF5000U Spectrofluorophotometer; SHIMADZU, Japan). A subset of cells was analyzed by flow cytometry (Coulter EPICS Elite ESP, Hialeah, Fla.). For spectrofluorometric analysis, excitation was at 488 nm and emission measured at 525 nm and 590 nm. Flow cytometry analysis was performed with an argon laser of single 488 nm as excitation, a filter transmitting 525±20 nm in FL1 channel, and a filter transmitting above 590 nm in FL2 channel. A minimum of 10,000 cells per sample was analyzed.

A statistical analysis was also performed. The mean ratios of red (593 nm) versus green (532 nm) fluorescence intensity peaks from spectroflourometry were compared across treatments. There were nine independent transfections per treatment. Differences were analyzed using Fisher's protected least significant difference.

Figure 5A:
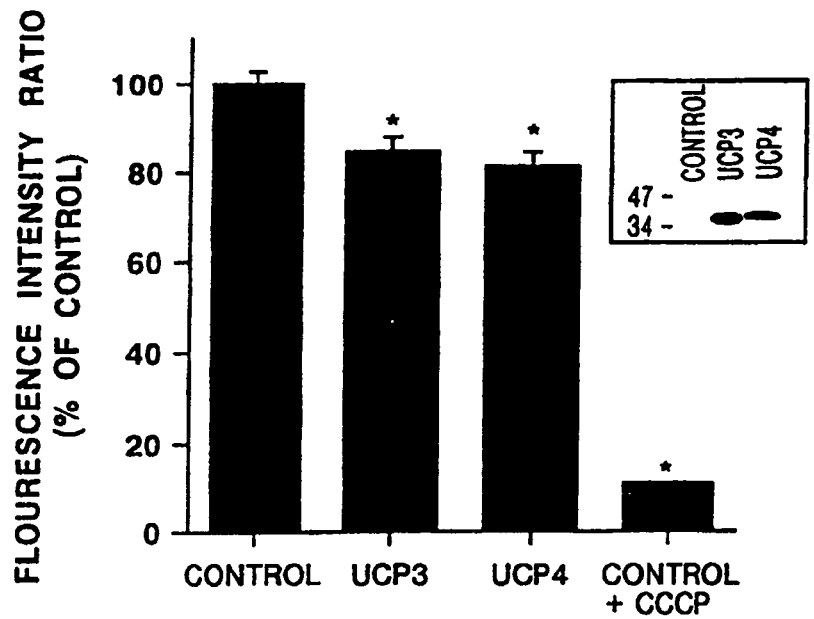
FIGS. 5A-5B show the results of in vitro assays conducted to determine the effects of UCP4 expression on mitochondrial membrane potential.
Figure 5B:
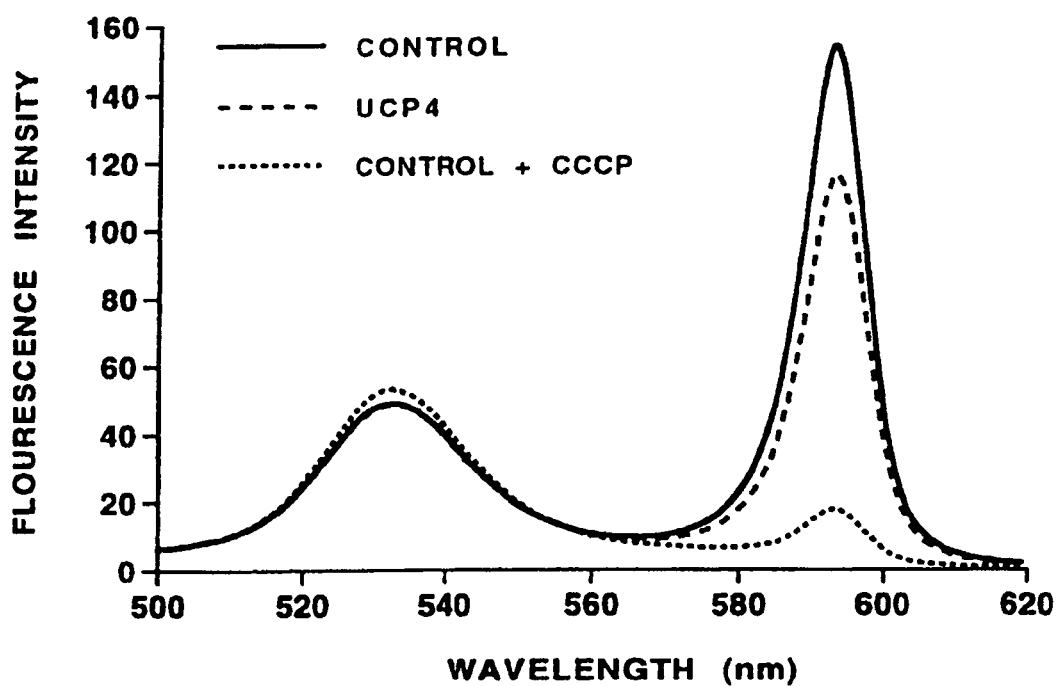
Figure 6A:
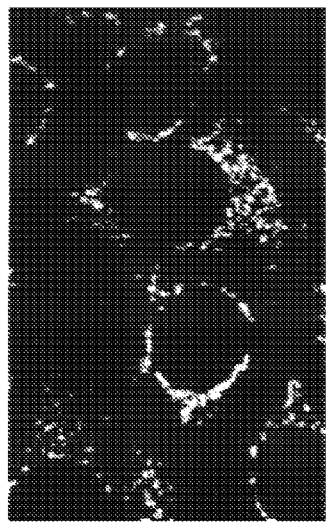
FIGS. 6A-6F show the results of in vitro assays conducted to determine the subcellular localization of UCP4.
Figure 6B:
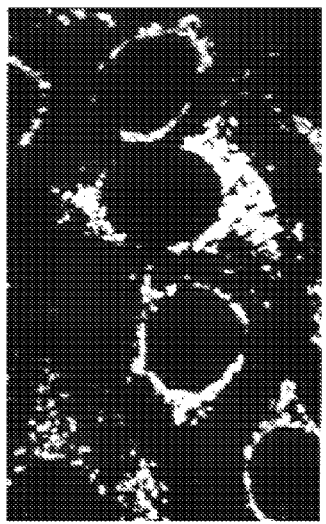
Figure 6C:
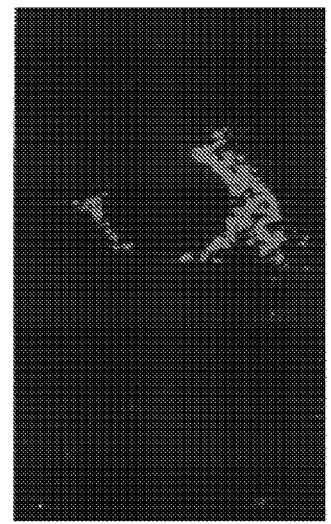
Figure 6D:
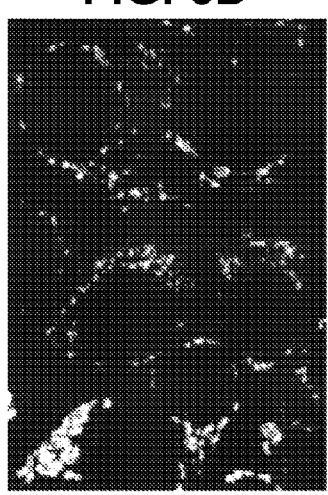
Figure 6E:
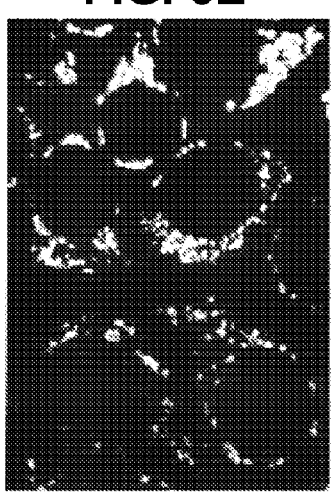
Figure 6F:
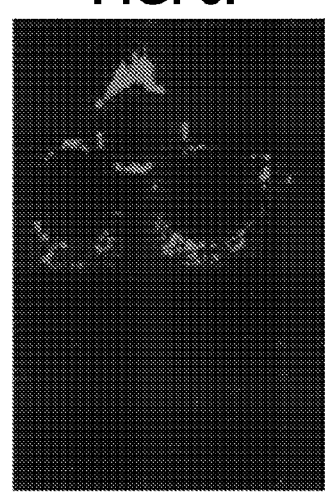

The results are illustrated in FIGS. 5A and 5B. Expression of UCP3 in the 293 cells reduced the fluorescent peak value ratio (593λ/532λ) by approximately 15% (n=3) in comparison with that of the vector control transfected cells, showing a decline in mitochondrial membrane potential. (FIG. 5A). In the cells transfected with UCP4, the fluorescence intensity indicative of membrane potential reduction decreased by 19% (n=6) in comparison with that of the vector control transfected cells. (FIGS. 5A and 5B). The $NH_2$-terminal Flag-tag had no effect on the activity of UCP3 or UCP4.

A FACs analysis also showed a similar decline in mitochondrial membrane potential. In the FACs analysis, the integrated red-to-green intensity ratios fell by 18% in UCP3-transfected cells and 24% in UCP4-transfected cells. Cells treated with the chemical uncoupler, CCCP, also showed a reduction of the red-to-green intensity ratio. (FIGS. 5A and 5B).

These data suggest that like UCP3, UCP4 has uncoupling activity.

Example 9

Preparation of Antibodies that Bind UCP4

This example illustrates preparation of monoclonal antibodies which can specifically bind UCP4.

Techniques for producing the monoclonal antibodies are known in the art and are described, for instance, in Goding, supra. Immunogens that may be employed include purified UCP4, fusion proteins containing UCP4, and cells expressing recombinant UCP4 on the cell surface. Selection of the immunogen can be made by the skilled artisan without undue experimentation.

Mice, such as Balb/c, are immunized with the UCP4 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemidal Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-UCP4 antibodies.

After a suitable antibody titer has been detected, the animals "positive" for antibodies can be injected with a final intravenous injection of UCP4. Three to four days later, the mice are sacrificed and the spleen cells are harvested. The spleen cells are then fused (using 35% polyethylene glycol) to a selected murine myeloma cell line such as P3x63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against UCP4. Determination of "positive" hybridoma cells secreting the desired monoclonal antibodies against UCP4 is within the skill in the art.

The positive hybridoma cells can be injected intraperitoneally into syngeneic Balb/c mice to produce ascites containing the anti-UCP4 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 10

Subcellular Localization

To examine the subcellular location of UCP4, human breast carcinoma MCF7 cells (ATCC HTB 22) were transfected with either pcDNA3Flag-UCP3 (prepared according to Example 8) or pcDNA3Flag-UCP4 (prepared according to Example 1) using FuGene transfection reagent (Boehringer Mannheim). The transfected cells were fixed in 3% formaldehyde at room temperature for 15 minutes and permeabilized with 1% TritonX-100 for 15 minutes. The cells were incubated with anti-Flag monoclonal antibody (10 µg/ml; Kodak) and anti-cytochrome C oxidase antibody (a mitochondrial marker) (3 ng/ml) for 20 minutes. The cells were then washed and incubated with Cy3™-conjugated (donkey anti-mouse; Jackson Laboratories) and FITC-conjugated (donkey anti-rabbit, Jackson Laboratories) secondary antibodies. The cells were then examined by fluorescence microscopy.

FIGS. 6A-6F show that UCP3 and UCP4 were co-localized with the mitochondrial marker.

Example 11

The Expression of UCP4 mRNA in Mice Subjected to Food and Temperature Stresses

To evaluate whether UCP4 has uncoupling activity in situ important to metabolism, the amount of UCP4 mRNA produced in tissues of mice that were subjected to food and temperature stresses, i.e., metabolic challenges, was determined. Depending on the role UCP4 may have in metabolism, the amount of UCP4 mRNA produced in a tissue may vary with stresses to metabolism such as fasting, fat consumption, and exposure to temperatures below room temperature.

The mice in this study were fed normal rodent chow (Purina Rodent Chow 5010; Purina, St. Louis, Mo.) and water ad libitum unless indicated otherwise. The type of mouse studied varied depending on the condition used to challenge the metabolism of the mouse studied and will be described below.

Generally, the mice studied were exposed to light 12 hours a day from 6:00 a.m. until 6:00 p.m. at which time they were exposed to dark for the following 12 hours.

The mice were sacrificed under $CO_2$ just prior to tissue harvest, which occurred in the morning between 8:00 and 12:00 a.m. unless specified otherwise. The tissues were harvested and total tissue RNA was prepared using reagents and protocols from Biotecx Lab, Houston, Tex. Although a number of tissues were collected from each mouse, the study focused on measuring the abundance of UCP4 mRNA in the brain (because the brain has high UCP4 gene expression). At least 5 mice/treatment were used in the studies.

Quantitative reverse-transcriptase polymerase chain reaction (RT-PCR) was used to determine the amount of UCP4 mRNA in the harvested tissues. RT-PCR was performed using mRNA samples. [Heid et al., *Genome Research*, 6:986-994 (1996); Gibson et al., *Genome Research*, 6:995-1001 (1996)]. Generally, to carry out quantitative RT-PCR, primers and probes specific to UCP4 were used (TaqMan Instrument, PE Biosciences, Foster City, Calif.). Values were corrected for mRNA loading using β-actin mRNA abundance as loading control. The following primers and probes were used:

For UCP4:

```
forward primer:
                                          (SEQ ID NO: 10)
5'AAT GCC TAT CGC CGA GGA G3';

reverse primer:
                                          (SEQ ID NO: 11)
5'GTA GGA ACT TGC TCG TCC GG3';

probe:
                                          (SEQ ID NO: 12)
5'(FAM)TGC TCG CGC TCA CGC AGA GAT G (TAMARA )3'.
```

For beta-actin:

```
forward primer:
                                          (SEQ ID NO: 13)
5'GAA ATC GTG CGT GAC ATC AAA GAG3';

reverse primer:
                                          (SEQ ID NO: 14)
5'CTC CTT CTG CAT CCT GTC AGC AA3';

probe:
                                          (SEQ ID NO: 15)
5'(FAM)CGG TTC CGA TGC CCT GAG GCT C (TAMARA) 3'.
```

The Effect of Food Consumption on UCP4 mRNA Expression

In a first study, seven-week old male mice (C57BL/6J; Bar Harbor, Me.) were studied to evaluate the effect of fasting and eating meals on UCP4 mRNA production in the mice studied. The mice were obtained at six weeks of age and at seven weeks were randomly assigned to one of three groups: control mice fed ad lib, mice fasted for 24 hours, and mice fasted for 24 hours and then fed ad lib for 24 hours.

The mice were sacrificed as described above after ad lib feeding for the first group, after 24 hours of fasting for the second group, and after the 48 hours of first fasting and then ad lib feeding for the third group. The tissues were harvested as described above.

Quantitative RT-PCR was performed for the brain tissue according to the methods described above and the amount of UCP4 mRNA produced in the brain was quantified. Statistical differences across the groups were determined using a protected Fisher's least significant difference analysis (L. Ott, *An Introduction to Statistical Methods and Data Analysis*, 3rd Ed., Boston: PWS-Kent Publishing Co., 1988). The data presented in FIGS. 8A to 8C represent means+/−SEM.

Figure 8:
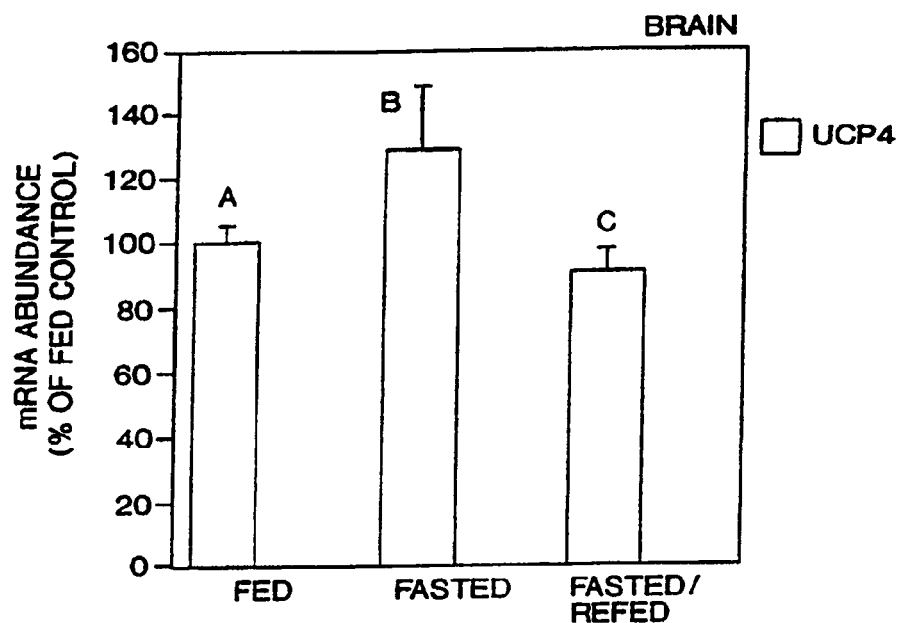
FIGS. 8A-8C show the results of in vitro assays conducted to determine the effect of food consumption on the expression of UCP4 mRNA.

FIG. 8A illustrates the UCP4 mRNA abundance in the brain tissue from mice that were fed ad lib for 24 hours. FIG. 8B illustrates the UCP4 mRNA abundance in the brain tissue from mice that fasted. FIG. 8C illustrates the UCP4 mRNA abundance in the brain tissue from mice that fasted for 24 hours and then were fed ad lib for 24 hours.

Typically, fasting and restriction of food consumption decrease metabolic rate, suggesting that expression of UCP4 mRNA would decrease for mice that were fasting compared to mice that were fed ad lib. Yet FIG. 8B does not show a decrease in UCP4 mRNA expression in brain tissue for the mice that fasted compared to the mice that were fed ad lib as shown in FIG. 8A.

The Effect of Fat Consumption on UCP4 mRNA Expression

In a second study, four-week old male mice (A/J or C57BL/6J; Jackson Labs, Bar Harbor, Me.) were studied to evaluate the effect of high and low fat diets on UCP4 mRNA production in the mice studied. A/J mice have been shown to be "obesity-resistant" on a high fat diet compared to "obesity-prone" C57BL6/J (see Surwit et al., supra). This may be due to a lower metabolic efficiency in the A/J strain—i.e., they apparently put on fewer calories per calories ingested.

The mice were obtained at four weeks of age and immediately placed on either a low fat diet or high fat diet (Research Diets, Inc., New Brunswick, N.J.) patterned after those formulated by Surwit et al., *Metabolism,* 44(5): 645-651 (1995), containing 11% or 58% fat (% calories), respectively. Animals were fed ad lib for approximately three weeks (days 22-23 on diet). They were then sacrificed, and their tissues were harvested as described above. Quantitative RT-PCR was performed for the brain tissue according to the methods described above and the amount of UCP4 mRNA produced in the brain tissue was quantified. Statistical differences across the groups were determined using a protected Fisher's least significant difference analysis (L. Ott, *An Introduction to Statistical Methods and Data Analysis,* 3rd Ed., Boston: PWS-Kent Publishing Co., 1988). The data presented in FIGS. 9A to 9D represent means+/−SEM.

Figure 9:
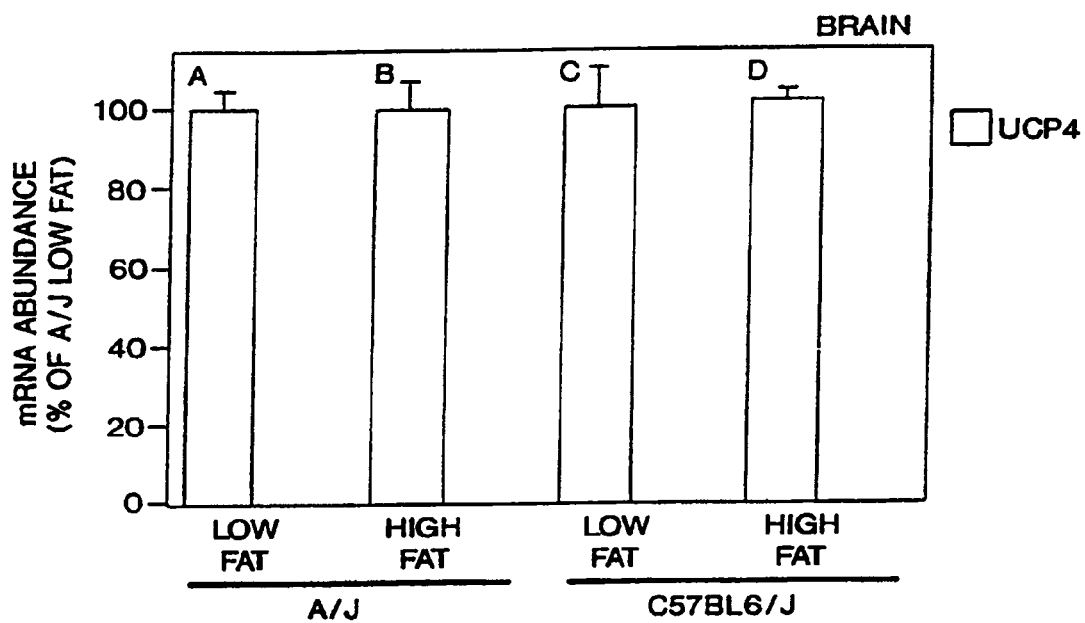
FIGS. 9A-9D show the results of in vitro assays conducted 30 to determine the effect of fat consumption on the expression of UCP4 mRNA.

FIG. 9A illustrates the UCP4 mRNA abundance in brain tissue from A/J mice that were fed a low fat diet, and FIG. 9B illustrates the UCP4 mRNA abundance in brain tissue from A/J mice that were fed a high fat diet. FIG. 9C illustrates the UCP4 mRNA abundance in brain tissue from C57BL6/J mice that were fed a low fat diet, and FIG. 9D illustrates the UCP4 mRNA abundance in brain tissue from C57BL6/J mice that were fed a high fat diet.

The Effect of Temperature Stress on UCP4

In a third study, male mice (FVB-N; Taconic, Germantown, N.Y.) were studied to evaluate the effect of exposing the mice to temperature stresses. Typically, cold exposure in rodents elicits an increase in metabolic rate. This metabolic increase may be to support a stable body temperature. Yet warm-acclamation, which is defined as chronic exposure to temperatures within the murine thermoneutral zone (approx. 30-35° C.), lowers metabolic rate. [Klaus et al., *Am. J. Physiol.,* 274:R287-R293 (1998)].

The mice in this study were housed two per cage and were randomly assigned to the following groups: a control group (housed at 22° C. for 3 weeks), a warm-acclimated group (housed at 33° C. for 3 weeks), a food-restricted group (housed at 22° C. for 3 weeks but given access each day to the average amount of food eaten by warm-acclimated mice the day before), a cold-challenged group (housed at 22° C. for 3 weeks prior to the initiation of exposure to 4° C.). For the cold-challenged mice, beginning in the morning, mice were exposed to 4° C. by being placed into a 4° C. room for 1, 6, 24, or 48 hours prior to sacrificing the mice and harvesting the tissue.

The mice were sacrificed and tissues were harvested at six week of age as described above. Quantitative RT-PCR was performed for the brain tissue according to the methods described above and the amount of UCP4 mRNA produced in the brain was quantified. Statistical differences across the groups were determined using a protected Fisher's least significant difference analysis (L. Ott, *An Introduction to Statistical Methods and Data Analysis,* 3rd Ed., Boston: PWS-Kent Publishing Co., 1988). The data presented in FIGS. 10A to 10G represent +/−SEM. An asterisk indicates a statistical difference of at least p<0.05.

Figure 10:
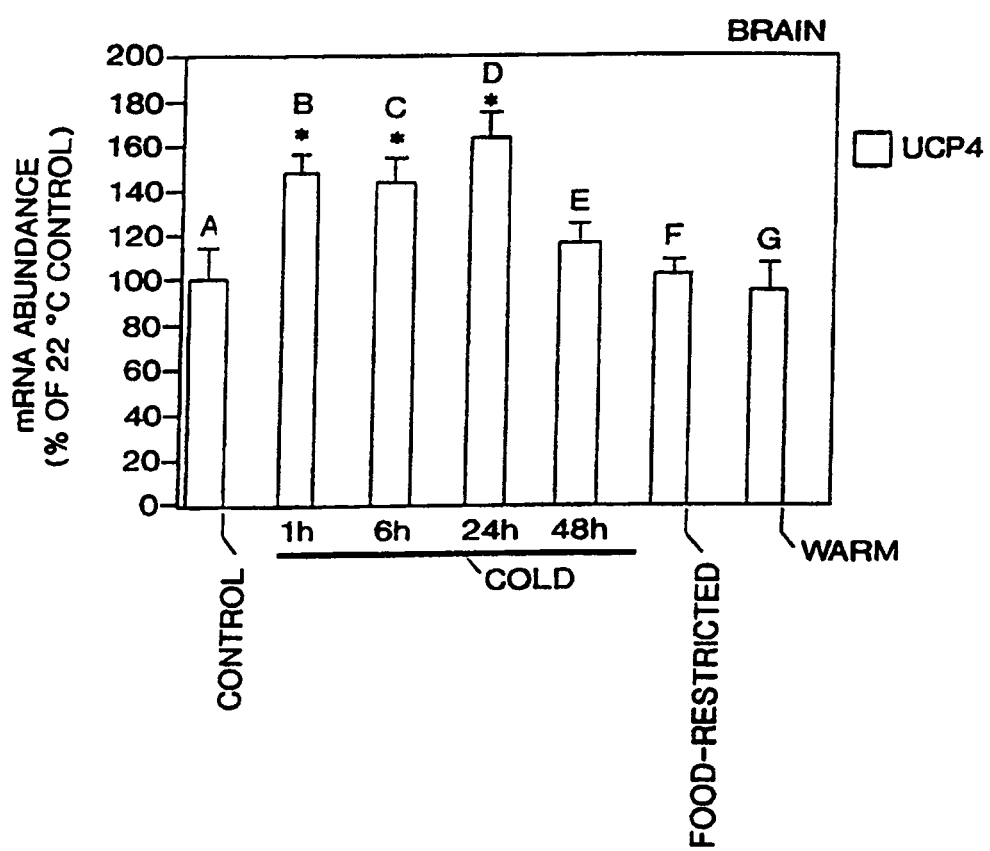
FIGS. 10A-10G show the results of in vitro assays conducted to determine the effect of temperature stress on the expression of UCP4 mRNA.

FIG. 10A illustrates the UCP4 mRNA abundance in the control group of mice. FIGS. 10B to 10E illustrate the UCP4 mRNA abundance in the group of mice that were cold-challenged for 1, 6, 24, and 48 hours, respectively. FIG. 10F illustrates the UCP4 mRNA abundance in the food-restricted group of mice, and FIG. 10G illustrates the UCP4 mRNA abundance in the warm-acclimated group of mice.

FIGS. 10B through 10E all indicate an increase in UCP4 mRNA expression in the cold-challenged mice compared to the control group shown in FIG. 10A. FIGS. 10F and 10G do not show a similar increase in UCP4 mRNA expression for the food-restricted mice and the warm-acclimated mice, respectively, compared to the control group shown in FIG. 10A.

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| DNA77568-1626 | 203134 | Aug. 18, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC '122 and the Commissioner's rules pursuant thereto (including 37 CFR '1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody which binds to a UCP4 polypeptide comprising amino acid residues 1 to 323 of FIG. 1 (SEQ ID:1), wherein the antibody is a monoclonal antibody.

2. The antibody of claim 1, wherein the antibody is a human antibody.

3. The antibody of claim 1, wherein the antibody is a humanized antibody.

4. The antibody of claim 1, wherein the antibody is a heteroconjugate antibody.

5. The antibody of claim 1, wherein the antibody consists of an Fv, Fab, Fab' or F(ab')$_2$ antibody.

6. The antibody of claim 1, wherein the antibody can be labeled with a detectable moiety.

7. An isolated antibody which specifically binds to a UCP4 polypeptide consisting essentially of amino acid residues 1 to 323 of FIG. 1 (SEQ ID:1), wherein the antibody is a monoclonal antibody.

8. The antibody of claim 7, wherein the antibody is a human antibody.

9. The antibody of claim 7, wherein the antibody is humanized antibody.

10. The antibody of claim 7, wherein the antibody is a heteroconjugate antibody.

11. The antibody of claim 7, wherein the antibody consists of an Fv, Fab, Fab' or F(ab')$_2$ antibody.

12. The antibody of claim 7, wherein the antibody can be labeled with a detectable moiety.

* * * * *

SEQUENCE LISTING

<160> NUMBER OF SEQ ID NOS: 18

<210> SEQ ID NO 1
<211> LENGTH: 323
<212> TYPE: PRT
<213> ORGANISM: Homo sapiens

<400> SEQUENCE: 1

```
Met Ser Val Pro Glu Glu Glu Arg Leu Leu Pro Leu Thr Gln Arg
 1               5                  10                  15

Trp Pro Arg Ala Ser Lys Phe Leu Leu Ser Gly Cys Ala Ala Thr Val
            20                  25                  30

Ala Glu Leu Ala Thr Phe Pro Leu Asp Leu Thr Lys Thr Arg Leu Gln
            35                  40                  45

Met Gln Gly Glu Ala Ala Leu Ala Arg Leu Gly Asp Gly Ala Arg Glu
        50                  55                  60

Ser Ala Pro Tyr Arg Gly Met Val Arg Thr Ala Leu Gly Ile Ile Glu
65                  70                  75                  80

Glu Glu Gly Phe Leu Lys Leu Trp Gln Gly Val Thr Pro Ala Ile Tyr
                85                  90                  95

Arg His Val Val Tyr Ser Gly Gly Arg Met Val Thr Tyr Glu His Leu
            100                 105                 110

Arg Glu Val Val Phe Gly Lys Ser Glu Asp Glu His Tyr Pro Leu Trp
```

|   |   |   | 115 |   |   |   | 120 |   |   |   | 125 |   |
|---|---|---|---|---|---|---|---|---|---|---|---|---|

Lys Ser Val Ile Gly Gly Met Met Ala Gly Val Ile Gly Gln Phe Leu
 130                 135                 140

Ala Asn Pro Thr Asp Leu Val Lys Val Gln Met Gln Met Glu Gly Lys
145                 150                 155                 160

Arg Lys Leu Glu Gly Lys Pro Leu Arg Phe Arg Gly Val His His Ala
                165                 170                 175

Phe Ala Lys Ile Leu Ala Glu Gly Gly Ile Arg Gly Leu Trp Ala Gly
            180                 185                 190

Trp Val Pro Asn Ile Gln Arg Ala Ala Leu Val Asn Met Gly Asp Leu
        195                 200                 205

Thr Thr Tyr Asp Thr Val Lys His Tyr Leu Val Leu Asn Thr Pro Leu
    210                 215                 220

Glu Asp Asn Ile Met Thr His Gly Leu Ser Ser Leu Cys Ser Gly Leu
225                 230                 235                 240

Val Ala Ser Ile Leu Gly Thr Pro Ala Asp Val Ile Lys Ser Arg Ile
                245                 250                 255

Met Asn Gln Pro Arg Asp Lys Gln Gly Arg Gly Leu Leu Tyr Lys Ser
            260                 265                 270

Ser Thr Asp Cys Leu Ile Gln Ala Val Gln Gly Glu Gly Phe Met Ser
        275                 280                 285

Leu Tyr Lys Gly Phe Leu Pro Ser Trp Leu Arg Met Thr Pro Trp Ser
    290                 295                 300

Met Val Phe Trp Leu Thr Tyr Glu Lys Ile Arg Glu Met Ser Gly Val
305                 310                 315                 320

Ser Pro Phe

<210> SEQ ID NO 2
<211> LENGTH: 1039
<212> TYPE: DNA
<213> ORGANISM: Homo sapiens

<400> SEQUENCE: 2
ccgagctcgg atcccgttat cgtcttgcgc tactgctgaa tgtccgtccc ggaggaggag      60
gagaggcttt tgccgctgac ccagagatgg ccccgagcga gcaaattcct actgtccggc     120
tgcgcggcta ccgtggccga gctagcaacc tttcccctgg atctcacaaa aactcgactc     180
caaatgcaag gagaagcagc tcttgctcgg ttgggagacg gtgcaagaga atctgccccc     240 tatagggaa tggtgcgcac agccctaggg atcattgaag aggaaggctt tctaaagctt     300
tggcaaggag tgacacccgc catttacaga cacgtagtgt attctggagg tcgaatggtc     360
acatatgaac atctccgaga ggttgtgttt ggcaaaagtg aagatgagca ttatcccctt     420
tggaaatcag tcattggagg gatgatggct ggtgttattg gccagttttt agccaatcca     480
actgacctag tgaaggttca gatgcaaatg gaaggaaaaa ggaactgga aggaaaacca     540 ttgcgatttc gtggtgtaca tcatgcattt gcaaaatct agctgaagg aggaatacga     600 gggctttggg caggctgggt acccaatata caaagagcag cactggtgaa tatgggagat     660
ttaaccactt atgatacagt gaaacactac ttggtattga atacaccact tgaggacaat     720
atcatgactc acggtttatc aagtttatgt tctggactgg tagcttctat tctgggaaca     780
ccagccgatg tcatcaaaag cagaataatg aatcaaccac gagataaaca ggaaggggga     840
cttttgtata atcatcgac tgactgcttg attcaggctg ttcaaggtga aggattcatg     900
agtctatata aaggcttttt accatcttgg ctgagaatga ccccttggtc aatggtgttc     960

-continued

```
tggcttactt atgaaaaaat cagagagatg agtggagtca gtccatttta agaattctgc    1020
agatatccat cacactggc                                                 1039
```

<210> SEQ ID NO 3
<211> LENGTH: 31
<212> TYPE: DNA
<213> ORGANISM: Artificial Sequence
<220> FEATURE:
<223> OTHER INFORMATION: Sequence is synthesized

<400> SEQUENCE: 3

```
cgcggatccc gttatcgtct tgcgctactg c                                   31
```

<210> SEQ ID NO 4
<211> LENGTH: 34
<212> TYPE: DNA
<213> ORGANISM: Artificial Sequence
<220> FEATURE:
<223> OTHER INFORMATION: reverse primer

<400> SEQUENCE: 4

```
gcggaattct aaaatggac tgactccact catc                                 34
```

<210> SEQ ID NO 5
<211> LENGTH: 1248
<212> TYPE: DNA
<213> ORGANISM: Artificial Sequence
<220> FEATURE:
<223> OTHER INFORMATION: Sequence is synthesized
<220> FEATURE:
<221> NAME/KEY: unsure
<222> LOCATION: (1231)...(1231)
<223> OTHER INFORMATION: unknown base

<400> SEQUENCE: 5

```
cgttatcgtc ttgcgctact gctgaatgtc cgtcccggag gaggaggaga ggcttttgcc    60
gctgacccag agatggcccc gagcgagcaa attcctactg tccggctgcg cggctaccgt    120
ggccgagcta gcaaccttc ccctggatct cacaaaaact cgactccaaa tgcaaggaga    180
agcagctctt gctcggttgg gagacggtgc aagagaatct gccccctata ggggaatggt    240
gcgcacagcc ctagggatca ttgaagagga aggcttttcta aagctttggc aaggagtgac    300
acccgccatt tacagacacg tagttatttc tggaggtcga atggtcacat atgaacatct    360
ccgagaggtt gtgtttggca aaagtgaaga tgagcattat ccccttggaa aatcagtcat    420 tggagggat atggctggtg ttattggcca gttttttagcc aatccaactg acctagtgaa    480
ggttcagatg caaatggaag gaaaaaggaa actggaagga aaaccattgc gatttcgtgg    540
tgtacatcat gcatttgcaa aaatcttagc tgaaggagga tacgaaggc tttgggcagg    600 ctgggtaccc aatatacaaa gagcagcact ggtgaatatg ggagatttaa ccacttatga    660
tacagtgaaa cactacttgg tattgaatac accacttgag gacaatatca tgactcacgg    720
tttatcaagt ttatgttctg gactggtagc ttctattctg gaacaccagg ccgatgtcat    780
caaaagcaga ataatgaatc aaccacgaga taaacaagga aggggacttt tgtataaatc    840
atcgactgac tgcttgattc aggctgttca aggtgaagga ttcatgagtc tatataagg    900 ctttttacca tcttggctga gaatgacccc ttggtcaatg gtgttctggc ttacttatga    960
aaaaatcaga gagatgaagtg gagtcagtcc atttttaaacc cctaaagatg caaccttaa    1020 agatacagtg ttcagtatta ttgaaatatg ggcatctgca acacatacccc ctatttattt    1080 ctacctcttt aggaagacac ctattccaca gagactgatt tatagggggc agcactttat    1140
```

```
tttttttctgg aaacccaagt tctctttgac tcctctttttt gtccaaaagt gatctggtcg    1200
gatctcacaa ggccatccaa tgagaccccg nacagcattt tctaaaga               1248
```

<210> SEQ ID NO 6
<211> LENGTH: 58
<212> TYPE: DNA
<213> ORGANISM: Artificial Sequence
<220> FEATURE:
<223> OTHER INFORMATION: Sequence is synthesized

<400> SEQUENCE: 6

```
cgcggatccg aaatggacta caaggacgac gatgacaagt ccgtcccgga ggaggag        58
```

<210> SEQ ID NO 7
<211> LENGTH: 35
<212> TYPE: DNA
<213> ORGANISM: Artificial Sequence
<220> FEATURE:
<223> OTHER INFORMATION: Sequence is synthesized

<400> SEQUENCE: 7

```
gcgaagcttg ccatggttgg actgaagcct tcaga                                35
```

<210> SEQ ID NO 8
<211> LENGTH: 33
<212> TYPE: DNA
<213> ORGANISM: Artificial Sequence
<220> FEATURE:
<223> OTHER INFORMATION: reverse primer

<400> SEQUENCE: 8

```
cgcgaattct caaaacggtg attcccgtaa cat                                  33
```

<210> SEQ ID NO 9
<211> LENGTH: 61
<212> TYPE: DNA
<213> ORGANISM: Artificial Sequence
<220> FEATURE:
<223> OTHER INFORMATION: Sequence is synthesized

<400> SEQUENCE: 9

```
gcgaagcttg ccatggacta caaggacgac gatgacaagg ttggactgaa gccttcagac    60
g                                                                     61
```

<210> SEQ ID NO 10
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 10

```
aatgcctatc gccgaggag                                                  19
```

<210> SEQ ID NO 11
<211> LENGTH: 20
<212> TYPE: DNA
<213> ORGANISM: Artificial Sequence
<220> FEATURE:
<223> OTHER INFORMATION: reverse primer

<400> SEQUENCE: 11

```
gtaggaactt gctcgtccgg                                                 20
```

<210> SEQ ID NO 12

```
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 12
tgctcgcgct cacgcagaga tg                                              22

<210> SEQ ID NO 13
<211> LENGTH: 24
<212> TYPE: DNA
<213> ORGANISM: Artificial Sequence
<220> FEATURE:
<223> OTHER INFORMATION: Sequence is synthesized

<400> SEQUENCE: 13
gaaatcgtgc gtgacatcaa agag                                            24

<210> SEQ ID NO 14
<211> LENGTH: 23
<212> TYPE: DNA
<213> ORGANISM: Artificial Sequence
<220> FEATURE:
<223> OTHER INFORMATION: reverse primer

<400> SEQUENCE: 14
ctccttctgc atcctgtcag caa                                             23

<210> SEQ ID NO 15
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 15
cggttccgat gccctgaggc tc                                              22

<210> SEQ ID NO 16
<211> LENGTH: 307
<212> TYPE: PRT
<213> ORGANISM: Homo sapiens

<400> SEQUENCE: 16

Met Gly Gly Leu Thr Ala Ser Asp Val His Pro Thr Leu Gly Val Gln
  1               5                  10                  15

Leu Phe Ser Ala Pro Ile Ala Ala Cys Leu Ala Asp Val Ile Thr Phe
                 20                  25                  30

Pro Leu Asp Thr Ala Lys Val Arg Leu Gln Val Gln Gly Glu Cys Pro
             35                  40                  45

Thr Ser Ser Val Ile Arg Tyr Lys Gly Val Leu Gly Thr Ile Thr Ala
         50                  55                  60

Val Val Lys Thr Glu Gly Arg Met Lys Leu Tyr Ser Gly Leu Pro Ala
 65                  70                  75                  80

Gly Leu Gln Arg Gln Ile Ser Ser Ala Ser Leu Arg Ile Gly Leu Tyr
                 85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Gly Val Ala Val
        115                 120                 125

Phe Ile Gly Gln Pro Thr Glu Val Val Lys Val Arg Leu Gln Ala Gln
    130                 135                 140
```

```
Ser His Leu His Gly Ile Lys Pro Arg Tyr Thr Gly Thr Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
            180                 185                 190

Val Thr Tyr Asp Leu Met Lys Glu Ala Phe Val Lys Asn Asn Ile Leu
        195                 200                 205

Ala Asp Asp Val Pro Cys His Leu Val Ser Ala Leu Ile Ala Gly Phe
    210                 215                 220

Cys Ala Thr Ala Met Ser Ser Pro Val Asp Val Lys Thr Arg Phe
225                 230                 235                 240

Ile Asn Ser Pro Pro Gly Gln Tyr Lys Ser Val Pro Asn Cys Ala Met
                245                 250                 255

Lys Val Phe Thr Asn Glu Gly Pro Thr Ala Phe Phe Lys Gly Leu Val
            260                 265                 270

Pro Ser Phe Leu Arg Leu Gly Ser Trp Asn Val Ile Met Phe Val Cys
        275                 280                 285

Phe Glu Gln Leu Lys Arg Glu Leu Ser Lys Ser Arg Gln Thr Met Asp
290                 295                 300

Cys Ala Thr
305

<210> SEQ ID NO 17
<211> LENGTH: 309
<212> TYPE: PRT
<213> ORGANISM: Homo sapiens

<400> SEQUENCE: 17

Met Val Gly Phe Lys Ala Thr Asp Val Pro Thr Ala Thr Val Lys
1               5                   10                  15

Phe Leu Gly Ala Gly Thr Ala Ala Cys Ile Ala Asp Leu Ile Thr Phe
                20                  25                  30

Pro Leu Asp Thr Ala Lys Val Arg Leu Gln Ile Gln Gly Glu Ser Gln
            35                  40                  45

Gly Pro Val Arg Ala Thr Val Ser Ala Gln Tyr Arg Gly Val Met Gly
50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Gln Met Ser Phe Ala Ser Val Arg
                85                  90                  95

Ile Gly Leu Tyr Asp Ser Val Lys Gln Phe Tyr Thr Lys Gly Ser Glu
            100                 105                 110

His Ala Ser Ile Gly Ser Arg Leu Leu Ala Gly Ser Thr Thr Gly Ala
        115                 120                 125

Leu Ala Val Ala Val Ala Gln Pro Thr Asp Val Val Lys Val Arg Phe
130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
            180                 185                 190

Glu Leu Val Thr Tyr Asp Leu Ile Lys Asp Ala Leu Leu Lys Ala Asn
        195                 200                 205
```

```
Leu Met Thr Asp Asp Leu Pro Cys His Phe Thr Ser Ala Phe Gly Ala
    210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
                260                 265                 270

Phe Met Pro Ser Phe Leu Arg Leu Gly Ser Trp Asn Val Val Met Phe
            275                 280                 285

Val Thr Tyr Glu Gln Leu Lys Arg Ala Leu Met Ala Ala Cys Thr Ser
290                 295                 300

Arg Glu Ala Pro Phe
305

<210> SEQ ID NO 18
<211> LENGTH: 300
<212> TYPE: PRT
<213> ORGANISM: Homo sapiens

<400> SEQUENCE: 18

Met Ala Val Lys Phe Leu Gly Ala Gly Thr Ala Ala Cys Phe Ala Asp
1               5                   10                  15

Leu Val Thr Phe Pro Leu Asp Thr Ala Lys Val Arg Leu Gln Ile Gln
            20                  25                  30

Gly Glu Asn Gln Ala Val Gln Thr Ala Arg Leu Val Gln Tyr Arg Gly
        35                  40                  45

Val Leu Gly Thr Ile Leu Thr Met Val Arg Thr Glu Gly Pro Cys Ser
    50                  55                  60

Pro Tyr Asn Gly Leu Val Ala Gly Leu Gln Arg Gln Met Ser Phe Ala
65                  70                  75                  80

Ser Ile Arg Ile Gly Leu Tyr Asp Ser Val Lys Gln Val Tyr Thr Pro
                85                  90                  95

Lys Gly Ala Asp Asn Ser Ser Leu Thr Thr Arg Ile Leu Ala Gly Cys
            100                 105                 110

Thr Thr Gly Ala Met Ala Val Thr Cys Ala Gln Pro Thr Asp Val Val
        115                 120                 125

Lys Val Arg Phe Gln Ala Ser Ile His Leu Gly Pro Ser Arg Ser Asp
130                 135                 140

Arg Lys Tyr Ser Gly Thr Met Asp Ala Tyr Arg Thr Ile Ala Arg Glu
145                 150                 155                 160

Glu Gly Val Arg Gly Leu Trp Lys Gly Thr Leu Pro Asn Ile Met Arg
                165                 170                 175

Asn Ala Ile Val Asn Cys Ala Glu Val Val Thr Tyr Asp Ile Leu Lys
            180                 185                 190

Glu Lys Leu Leu Asp Tyr His Leu Leu Thr Asp Asn Phe Pro Cys His
        195                 200                 205

Phe Val Ser Ala Phe Gly Ala Gly Phe Cys Ala Thr Val Val Ala Ser
    210                 215                 220

Pro Val Asp Val Val Lys Thr Arg Tyr Met Asn Ser Pro Pro Gly Gln
225                 230                 235                 240

Tyr Phe Ser Pro Leu Asp Cys Met Ile Lys Met Val Ala Gln Glu Gly
                245                 250                 255

Pro Thr Ala Phe Tyr Lys Gly Phe Thr Pro Ser Phe Leu Arg Leu Gly
            260                 265                 270
```

```
Ser Trp Asn Val Val Met Phe Val Thr Tyr Glu Gln Leu Lys Arg Ala
            275                 280                 285
Leu Met Lys Val Gln Met Leu Arg Glu Ser Pro Phe
    290                 295                 300
```